(12) United States Patent
Pantages et al.

(10) Patent No.: US 12,661,119 B2
(45) Date of Patent: Jun. 23, 2026

(54) DUAL PURPOSE INDUCTORS FOR IMPLANTABLE MEDICAL DEVICES AND ASSOCIATED SYSTEMS AND METHODS

(71) Applicant: Shifamed Holdings, LLC, Campbell, CA (US)

(72) Inventors: Anthony Pantages, San Jose, CA (US); Peter Andriola, Castro Valley, CA (US); Brian Fahey, Menlo Park, CA (US); Scott Robertson, Portland, OR (US); Miles Alexander, Fremont, CA (US); Soane Eke, East Palo Alto, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 371 days.

(21) Appl. No.: 18/247,924

(22) PCT Filed: Oct. 15, 2021

(86) PCT No.: PCT/US2021/055191

§ 371 (c)(1),
(2) Date: Apr. 5, 2023

(87) PCT Pub. No.: WO2022/081980

PCT Pub. Date: Apr. 21, 2022

(65) Prior Publication Data

US 2023/0371953 A1 Nov. 23, 2023

Related U.S. Application Data

(60) Provisional application No. 63/093,073, filed on Oct. 16, 2020.

(51) Int. Cl.

| | |
|---|---|
| ***A61B 17/11*** | (2006.01) |
| ***A61B 17/00*** | (2006.01) |
| ***A61M 27/00*** | (2006.01) |

(52) U.S. Cl.
CPC ........ *A61B 17/11* (2013.01); *A61B 17/00234* (2013.01); *A61M 27/002* (2013.01);
(Continued)

(58) Field of Classification Search
CPC .............. A61B 17/11; A61B 17/00234; A61B 2017/00039; A61B 2017/00243;
(Continued)

(56) References Cited

U.S. PATENT DOCUMENTS

| | | | |
|---|---|---|---|
| 3,874,388 | A | 4/1975 | King et al. |
| 4,601,309 | A | 7/1986 | Chang |

(Continued)

FOREIGN PATENT DOCUMENTS

| | | |
|---|---|---|
| AU | 2005211243 | 8/2005 |
| AU | 2010344182 | 8/2012 |

(Continued)

OTHER PUBLICATIONS

Jodi Perkins, "Corvia Medical and physIQ Partner in Global Phase 3 Heart Failure Clinical Trial to Leverage Novel Digital Endpoints," Press Release, 2019 Copyright, Medical Alley Association, 3 pages.

(Continued)

*Primary Examiner* — Adam Marcetich
(74) *Attorney, Agent, or Firm* — Perkins Coie LLP

(57) ABSTRACT

The present technology is directed to implantable medical devices comprising an electrical circuit for powering one or more active components of the device, such as an actuation element, an engine, or a sensor. The electrical circuit can include one or more inductors having a plurality of receiving coils that generate a current in response to being exposed to an electromagnetic field. The current generated by the receiving coils can be used to directly or indirectly power the one or more active components. The inductors can have one or more wires having a non-concentric configuration such (Continued)

that, in addition to generating the current for powering the device, the receiving coils also anchor a portion of the device when it is implanted. For example, the receiving coils can be at least partially composed of a superelastic material such that they exhibit superelastic properties at body temperature.

23 Claims, 6 Drawing Sheets

(52) U.S. Cl.
CPC .............. *A61B 2017/00039* (2013.01); *A61B 2017/00243* (2013.01); *A61B 2017/1139* (2013.01); *A61M 2205/04* (2013.01)

(58) Field of Classification Search
CPC .. A61B 2017/1139; A61B 2017/00022; A61B 2017/00221; A61B 2017/00398; A61B 2017/00411; A61B 2017/00867; A61M 27/002; A61M 2205/04
See application file for complete search history.

(56) References Cited

U.S. PATENT DOCUMENTS 4,662,355 A 5/1987 Pieronne et al.
4,705,507 A 11/1987 Boyles
4,836,204 A 6/1989 Landymore et al.
4,969,890 A 11/1990 Sugita et al.
4,979,955 A 12/1990 Smith
4,995,857 A 2/1991 Arnold
5,186,431 A 2/1993 Tamari
5,197,978 A 3/1993 Hess
5,267,940 A 12/1993 Moulder
5,290,227 A 3/1994 Pasque
5,312,341 A 5/1994 Turi
5,326,374 A 7/1994 Ilbawi et al.
5,332,402 A 7/1994 Teitelbaum
5,334,217 A 8/1994 Das
5,409,019 A 4/1995 Wilk
5,429,144 A 7/1995 Wilk
5,500,015 A 3/1996 Deac
5,531,759 A 7/1996 Kensey et al.
5,556,386 A 9/1996 Todd
5,584,803 A 12/1996 Stevens et al.
5,597,377 A 1/1997 Aldea
5,611,338 A 3/1997 Gallup
5,645,559 A 7/1997 Hachtman et al.
5,655,548 A 8/1997 Nelson et al.
5,662,711 A 9/1997 Douglas
5,702,412 A 12/1997 Popov et al.
5,725,552 A 3/1998 Kotula et al.
5,741,297 A 4/1998 Simon
5,795,307 A 8/1998 Krueger
5,810,836 A 9/1998 Hussein et al.
5,824,071 A 10/1998 Nelson et al.
5,916,193 A 6/1999 Stevens et al.
5,941,850 A 8/1999 Shah et al.
5,944,019 A 8/1999 Kundson et al.
5,957,949 A 9/1999 Leonhardt et al.
6,024,743 A 2/2000 Edwards
6,039,759 A 3/2000 Carpentier et al.
6,077,298 A 6/2000 Tu et al.
6,120,534 A 9/2000 Ruiz
6,126,686 A 10/2000 Badylak et al.
6,165,188 A 12/2000 Saadat et al.
6,165,209 A 12/2000 Patterson et al.
6,210,318 B1 4/2001 Lederman
6,217,541 B1 4/2001 Yu
6,240,322 B1 5/2001 Peterfeso et al.
6,242,762 B1 6/2001 Brown et al.
6,254,564 B1 7/2001 Wilk et al.
6,260,552 B1 7/2001 Mortier et al.
6,270,526 B1 8/2001 Cox
6,277,078 B1 8/2001 Porat et al.
6,302,892 B1 10/2001 Wilk
6,328,699 B1 12/2001 Eigler et al.
6,344,022 B1 2/2002 Jarvik
6,358,277 B1 3/2002 Duran
6,406,422 B1 6/2002 Landesberg
6,447,539 B1 9/2002 Nelson et al.
6,451,051 B2 9/2002 Drasler et al.
6,458,153 B1 10/2002 Bailey et al.
6,468,303 B1 10/2002 Amplatz et al.
6,478,776 B1 11/2002 Rosenman et al.
6,491,705 B2 12/2002 Gifford, III et al.
6,494,889 B1 12/2002 Fleischman et al.
6,514,285 B1 2/2003 Pinchasik
6,527,698 B1 3/2003 Kung et al.
6,544,208 B2 4/2003 Ethier et al.
6,562,066 B1 5/2003 Martin
6,572,652 B2 6/2003 Shaknovich
6,589,198 B1 7/2003 Soltanpour et al.
6,632,169 B2 10/2003 Korakianitis et al.
6,638,303 B1 10/2003 Campbell
6,641,610 B2 11/2003 Wolf et al.
6,652,578 B2 11/2003 Bailey et al.
6,685,664 B2 2/2004 Levin et al.
6,712,836 B1 3/2004 Berg et al.
6,783,499 B2 8/2004 Schwartz
6,909,920 B2 6/2005 Lokhoff et al.
6,911,043 B2 6/2005 Myers et al.
6,926,670 B2 8/2005 Rich et al.
7,001,409 B2 2/2006 Amplatz
7,011,095 B2 3/2006 Wolf et al.
7,056,294 B2 6/2006 Khairkhahan et al.
7,149,587 B2 12/2006 Wardle et al.
7,175,656 B2 2/2007 Khairkhahan
7,270,675 B2 9/2007 Chun et al.
7,294,115 B1 11/2007 Wilk
7,311,690 B2 12/2007 Burnett
7,311,730 B2 12/2007 Gabbay
7,317,951 B2 1/2008 Schneider et al.
7,389,134 B1 6/2008 Karicherla et al.
7,390,310 B2 6/2008 McCusker et al.
7,513,908 B2 4/2009 Lattouf
7,524,329 B2 4/2009 Rucker
7,524,330 B2 4/2009 Berreklouw
7,524,332 B2 4/2009 Osborne et al.
7,608,067 B2 10/2009 Bonn
7,615,010 B1 11/2009 Najafi et al.
7,617,001 B2 11/2009 Penner et al.
7,634,318 B2 12/2009 Tran et al.
7,658,747 B2 2/2010 Forde et al.
7,665,466 B2 2/2010 Figulla et al.
7,699,059 B2 4/2010 Fonseca et al.
7,736,327 B2 6/2010 Wilk et al.
7,780,725 B2 8/2010 Haug et al.
7,794,473 B2 9/2010 Tessmer et al.
7,806,921 B2 10/2010 Hoffman
7,860,579 B2 12/2010 Goetzinger et al.
7,892,246 B2 2/2011 Akin et al.
7,905,901 B2 3/2011 Corcoran et al.
7,922,764 B2 4/2011 Gordy et al.
7,938,840 B2 5/2011 Golden et al.
7,967,769 B2 6/2011 Faul et al.
7,988,724 B2 8/2011 Salahich et al.
8,012,198 B2 9/2011 Hill et al.
8,014,865 B2 9/2011 Najafi et al.
8,016,877 B2 9/2011 Seguin et al.
8,043,360 B2 10/2011 McNamara et al.
8,070,708 B2 12/2011 Rottenberg et al.
8,091,556 B2 1/2012 Keren et al.
8,096,959 B2 1/2012 Stewart et al.
8,147,545 B2 4/2012 Avior
8,157,860 B2 4/2012 McNamara et al.
8,172,896 B2 5/2012 McNamara et al.
8,235,916 B2 8/2012 Whiting et al.
8,235,933 B2 8/2012 Keren et al.
8,244,367 B2 8/2012 Wahlstrand et al.
8,246,677 B2 8/2012 Ryan
8,252,042 B2 8/2012 McNamara et al.

(56) References Cited

U.S. PATENT DOCUMENTS 8,255,062 B2 8/2012 Doan et al.
8,285,388 B2 10/2012 Wahlstrand
8,298,240 B2 10/2012 Giger et al.
8,303,511 B2 11/2012 Eigler et al.
8,328,751 B2 12/2012 Keren et al.
8,348,996 B2 1/2013 Tuval et al.
8,398,708 B2 3/2013 Meiri et al.
8,460,366 B2 6/2013 Rowe
8,460,372 B2 6/2013 McNamara et al.
8,597,225 B2 12/2013 Kapadia
8,644,933 B2 2/2014 Ozawa et al.
8,647,381 B2 2/2014 Essinger et al.
8,696,611 B2 4/2014 Nitzan et al.
8,696,693 B2 4/2014 Najafi et al.
8,740,962 B2 6/2014 Finch et al.
8,745,845 B2 6/2014 Finch et al.
8,747,458 B2 6/2014 Tuval et al.
8,752,258 B2 6/2014 Finch et al.
8,764,848 B2 7/2014 Callaghan et al.
8,781,596 B2 7/2014 Aghassian et al.
8,795,329 B2 8/2014 Forde et al.
8,827,888 B2 9/2014 Bolyard et al.
8,882,697 B2 11/2014 Celermajer et al.
8,932,247 B2 1/2015 Stergiopulos
8,951,223 B2 2/2015 McNamara et al.
D727,501 S 4/2015 Heipl
9,005,155 B2 4/2015 Sugimoto
9,034,034 B2 5/2015 Nitzan et al.
9,084,589 B2 7/2015 Moszner
9,138,213 B2 9/2015 Amin et al.
9,179,899 B2 11/2015 Freudenthal
9,180,005 B1 11/2015 Lashinski et al.
9,204,842 B2 12/2015 Mothilal et al.
9,205,236 B2 12/2015 McNamara et al.
9,232,997 B2 1/2016 Sugimoto et al.
9,277,995 B2 3/2016 Celermajer et al.
9,333,067 B2 5/2016 McKnight et al.
9,358,371 B2 6/2016 McNamara et al.
9,456,812 B2 10/2016 Finch et al.
9,610,041 B2 4/2017 Foster et al.
9,629,715 B2 4/2017 Nitzan et al.
9,642,993 B2 5/2017 McNamara et al.
9,649,480 B2 5/2017 Sugimoto et al.
9,681,948 B2 6/2017 Levi et al.
9,707,382 B2 7/2017 Nitzan et al.
9,713,696 B2 7/2017 Yacoby et al.
9,724,499 B2 8/2017 Rottenberg et al.
9,737,264 B2 8/2017 Braido et al.
9,757,107 B2 9/2017 McNamara et al.
9,775,636 B2 10/2017 Fazio et al.
9,789,294 B2 10/2017 Taft et al.
9,918,677 B2 3/2018 Eigler et al.
9,918,856 B2 3/2018 Favier et al.
9,937,036 B2 4/2018 Sugimoto et al.
9,943,670 B2 4/2018 Keren et al.
9,980,815 B2 5/2018 Nitzan et al.
10,045,766 B2 8/2018 McNamara et al.
10,076,403 B1 9/2018 Eigler et al.
10,098,551 B2 10/2018 Doan et al.
10,122,222 B2 11/2018 Hansen et al.
10,188,375 B2 1/2019 McNamara et al.
10,195,441 B2 2/2019 Kaiser et al.
10,207,087 B2 2/2019 Keren
10,251,740 B2 4/2019 Eigler et al.
10,292,690 B2 5/2019 Celermajer et al.
10,350,384 B2 7/2019 Farnan et al.
10,357,357 B2 7/2019 Levi et al.
10,368,981 B2 8/2019 Nitzan et al.
10,376,359 B2 8/2019 Essinger et al.
10,376,680 B2 8/2019 McNamara et al.
10,398,421 B2 9/2019 Celermajer
10,405,903 B1 9/2019 Biesinger et al.
10,413,284 B2 9/2019 McNamara et al.
10,413,286 B2 9/2019 McNamara et al.
10,463,477 B2 11/2019 Forcucci et al.
10,463,490 B2 11/2019 Rottenberg et al.
10,471,251 B1 11/2019 Manicka
10,478,067 B2 11/2019 Najafi
10,478,594 B2 11/2019 Yacoby et al.
10,568,751 B2 2/2020 McNamara
10,588,611 B2 3/2020 Magnin et al.
10,595,999 B2 3/2020 Vettukattil et al.
10,610,210 B2 4/2020 Finch et al.
10,624,621 B2 4/2020 Celermajer
10,632,292 B2 4/2020 Forcucci et al.
10,639,459 B2 5/2020 Nitzan et al.
10,667,896 B2 6/2020 Delaney, Jr. et al.
10,675,450 B2 6/2020 Finch
10,828,151 B2 11/2020 Nitzan et al.
10,835,394 B2 11/2020 Nae et al.
10,898,698 B1 1/2021 Eigler et al.
10,912,645 B2 2/2021 Rottenberg et al.
10,925,706 B2 2/2021 Eigler et al.
10,932,786 B2 3/2021 McNamara et al.
10,940,296 B2 3/2021 Keren
10,945,716 B2 3/2021 Chen et al.
11,135,410 B2 10/2021 Finch et al.
11,253,685 B2 2/2022 Fahey et al.
11,622,695 B1 4/2023 Andriola et al.
11,633,194 B2 4/2023 Alexander et al.
11,690,976 B2 7/2023 Yacoby et al.
11,801,369 B2 10/2023 Fahey et al.
11,813,386 B2 11/2023 Nae et al.
11,857,197 B2 1/2024 Alexander et al.
12,151,071 B2 11/2024 Fehey et al.
12,186,176 B2 1/2025 Eigler et al.
2002/0035396 A1* 3/2002 Heath .................. A61L 31/088 623/1.15
2002/0072656 A1 6/2002 Vantassel et al.
2002/0115991 A1 8/2002 Edwards
2002/0142119 A1 10/2002 Seward et al.
2002/0161427 A1 10/2002 Rabkin et al.
2002/0165606 A1 11/2002 Wolf et al.
2002/0169371 A1 11/2002 Gilderdale
2002/0169475 A1 11/2002 Gainor et al.
2002/0173742 A1 11/2002 Keren et al.
2002/0177891 A1 11/2002 Miles et al.
2003/0032967 A1 2/2003 Park et al.
2003/0120292 A1 6/2003 Park et al.
2003/0125798 A1 7/2003 Martin
2003/0127090 A1 7/2003 Gifford et al.
2004/0016514 A1 1/2004 Nien
2004/0077988 A1 4/2004 Tweden et al.
2004/0088045 A1 5/2004 Cox
2004/0093075 A1 5/2004 Kuehne
2004/0143294 A1 7/2004 Corcoran et al.
2004/0147869 A1 7/2004 Wolf et al.
2004/0147939 A1 7/2004 Rabkin et al.
2004/0158143 A1 8/2004 Flaherty et al.
2004/0162514 A1 8/2004 Alferness et al.
2004/0186566 A1 9/2004 Hindrichs et al.
2004/0210190 A1 10/2004 Kohler et al.
2004/0215067 A1 10/2004 Stiger et al.
2004/0215323 A1 10/2004 Stiger
2005/0004641 A1 1/2005 Pappu
2005/0033351 A1 2/2005 Newton
2005/0055082 A1 3/2005 Ben Muvhar et al.
2005/0060030 A1 3/2005 Lashinski et al.
2005/0101946 A1 5/2005 Govari et al.
2005/0143758 A1 6/2005 Abbott et al.
2005/0148925 A1 7/2005 Rottenberg et al.
2005/0159789 A1 7/2005 Brockway et al.
2005/0165344 A1 7/2005 Dobak, III
2005/0192627 A1 9/2005 Whisenant et al.
2005/0204811 A1 9/2005 Neff
2005/0251212 A1 11/2005 Kieval et al.
2005/0288722 A1 12/2005 Eigler et al.
2006/0009810 A1 1/2006 Mann et al.
2006/0025857 A1 2/2006 Bergheim et al.
2006/0047205 A1 3/2006 Ludomirsky et al.
2006/0111660 A1 5/2006 Wolf et al.
2006/0116625 A1 6/2006 Renati et al.
2006/0200030 A1 9/2006 White et al.

(56) References Cited

U.S. PATENT DOCUMENTS

2006/0287705 A1* 12/2006 Weber .................. G01R 33/288 623/1.15
2007/0010837 A1 1/2007 Tanaka
2007/0010852 A1 1/2007 Blaeser et al.
2007/0043435 A1 2/2007 Seguin et al.
2007/0073380 A1* 3/2007 Vazquez .................. A61F 2/90 623/1.15
2007/0088220 A1 4/2007 Stahmann
2007/0088223 A1 4/2007 Mann et al.
2007/0106336 A1* 5/2007 Schaer ................ A61N 1/3627 607/37
2007/0112344 A1 5/2007 Keilman
2007/0118039 A1 5/2007 Bodecker et al.
2007/0123917 A1 5/2007 Ortiz et al.
2007/0142907 A1* 6/2007 Moaddeb ............. A61F 2/2469 623/2.37
2007/0150019 A1 6/2007 Youker et al.
2007/0213813 A1 9/2007 Von Segesser et al.
2007/0282157 A1 12/2007 Rottenberg et al.
2008/0033527 A1 2/2008 Nunez et al.
2008/0081962 A1 4/2008 Miller et al.
2008/0097276 A1 4/2008 Bertrand et al.
2008/0108904 A1 5/2008 Heil
2008/0119891 A1 5/2008 Miles et al.
2008/0127689 A1 6/2008 McCusker et al.
2008/0171941 A1 7/2008 Huelskamp et al.
2008/0208083 A1 8/2008 Lin et al.
2008/0208286 A1 8/2008 Kieval et al.
2008/0215131 A1 9/2008 Magnuson et al.
2009/0036975 A1 2/2009 Ward et al.
2009/0204133 A1 8/2009 Melzer et al.
2009/0243956 A1 10/2009 Keilman et al.
2009/0270742 A1 10/2009 Wolinsky et al.
2009/0276040 A1 11/2009 Rowe et al.
2009/0281557 A1 11/2009 Sander et al.
2009/0281597 A1 11/2009 Parramon et al.
2010/0057192 A1 3/2010 Celermajer
2010/0063375 A1 3/2010 Kassab et al.
2010/0076366 A1 3/2010 Henderson, Sr. et al.
2010/0076517 A1 3/2010 Imran
2010/0106028 A1 4/2010 Penner et al.
2010/0106171 A1* 4/2010 Arepally ............... A61B 17/11 606/153
2010/0160906 A1 6/2010 Jarrard
2010/0168672 A1 7/2010 Carr
2010/0174201 A1* 7/2010 Bodecker ............. A61B 5/6882 600/488
2010/0179449 A1 7/2010 Chow et al.
2010/0241241 A1 9/2010 McKnight et al.
2010/0249560 A1 9/2010 Levinson et al.
2010/0256753 A1 10/2010 McNamara et al.
2010/0262021 A1 10/2010 Yadav et al.
2010/0262036 A1 10/2010 Najafi et al.
2010/0275592 A1 11/2010 Topliss et al.
2010/0298755 A1 11/2010 McNamara et al.
2010/0298930 A1 11/2010 Orlov
2011/0054515 A1 3/2011 Bridgeman et al.
2011/0082377 A1 4/2011 Ah
2011/0218480 A1 9/2011 Rottenberg et al.
2011/0218481 A1 9/2011 Rottenberg et al.
2011/0257723 A1 10/2011 McNamara
2011/0264194 A1 10/2011 Griswold
2011/0282217 A1 11/2011 Nashet
2011/0295183 A1 12/2011 Finch et al.
2011/0306916 A1 12/2011 Nitzan et al.
2012/0053686 A1 3/2012 McNamara et al.
2012/0130301 A1 5/2012 McNamara et al.
2012/0197392 A1 8/2012 DuMoutelle et al.
2012/0209375 A1 8/2012 Madrid et al.
2012/0215303 A1 8/2012 Quadri et al.
2012/0265296 A1 10/2012 McNamara et al.
2012/0283773 A1 11/2012 Van Tassel et al.
2012/0289776 A1* 11/2012 Keast ..................... A61B 5/062 600/114
2012/0290062 A1 11/2012 McNamara et al.
2013/0123569 A1 5/2013 Gross
2013/0144379 A1 6/2013 Najafi et al.
2013/0165967 A1 6/2013 Amin et al.
2013/0178783 A1 7/2013 Mcnamara et al.
2013/0178784 A1 7/2013 McNamara et al.
2013/0190799 A1 7/2013 Clark
2013/0192611 A1 8/2013 Taepke, II et al.
2013/0197423 A1 8/2013 Keren et al.
2013/0197607 A1 8/2013 Wilder et al.
2013/0211221 A1 8/2013 Sunnarborg et al.
2013/0253343 A1 9/2013 Waldhauser et al.
2013/0261531 A1 10/2013 Gallagher et al.
2014/0012342 A1 1/2014 Penner et al.
2014/0046427 A1 2/2014 Michalak
2014/0121750 A1 5/2014 Hadley et al.
2014/0128795 A1 5/2014 Karen et al.
2014/0128796 A1 5/2014 Keren et al.
2014/0135647 A1 5/2014 Wolf, II
2014/0155768 A1 6/2014 Orion et al.
2014/0163449 A1 6/2014 Rottenberg et al.
2014/0213959 A1 7/2014 Nitzan et al.
2014/0222040 A1 8/2014 Park et al.
2014/0222144 A1 8/2014 Eberhardt et al.
2014/0249616 A1 9/2014 Strauss et al.
2014/0277054 A1 9/2014 McNamara et al.
2014/0306807 A1 10/2014 Rowland et al.
2014/0324094 A1* 10/2014 Weber .................. A61B 5/0816 606/198
2015/0034217 A1 2/2015 Vad
2015/0039084 A1 2/2015 Levi et al.
2015/0112383 A1* 4/2015 Sherman ............ A61B 17/0057 606/213
2015/0119796 A1 4/2015 Finch
2015/0141807 A1 5/2015 Fetterly
2015/0148731 A1 5/2015 Mcnamara et al.
2015/0157268 A1 6/2015 Winshtein et al.
2015/0208929 A1 7/2015 Rowland et al.
2015/0223707 A1 8/2015 Ludoph et al.
2015/0230843 A1 8/2015 Palmer et al.
2015/0231387 A1 8/2015 Harding et al.
2015/0289929 A1 10/2015 Toth et al.
2015/0320424 A1 11/2015 Gourlay
2016/0022423 A1 1/2016 Mcnamara et al.
2016/0089079 A1 3/2016 Stein
2016/0135813 A1* 5/2016 Johnson ................. A61B 17/11 606/213
2016/0151179 A1 6/2016 Favier et al.
2016/0158561 A1 6/2016 Reddy
2016/0220357 A1 8/2016 Anand et al.
2016/0235999 A1 8/2016 Nuta et al.
2016/0302808 A1 10/2016 Loganathan et al.
2016/0374682 A1 12/2016 Leonard et al.
2017/0014067 A1 1/2017 Peppou et al.
2017/0105635 A1 4/2017 Cho et al.
2017/0113026 A1 4/2017 Finch
2017/0273788 A1* 9/2017 O'Carroll ............. A61F 2/2445
2017/0273790 A1 9/2017 Vettukattil et al.
2017/0312078 A1 11/2017 Krivoruchko
2017/0340460 A1 11/2017 Rosen et al.
2018/0014828 A1 1/2018 Fonte et al.
2018/0110468 A1 4/2018 Goldshtein et al.
2018/0117341 A1 5/2018 Kane et al.
2018/0161121 A1* 6/2018 Butler ................. A61M 25/005
2018/0168463 A1 6/2018 Morris et al.
2018/0243071 A1 8/2018 Eigler et al.
2018/0247095 A1 8/2018 Sundaram et al.
2018/0250014 A1 9/2018 Melanson et al.
2018/0256865 A1 9/2018 Finch et al.
2018/0262037 A1 9/2018 Meskeus
2018/0280667 A1 10/2018 Keren
2018/0296375 A1 10/2018 Van Langenhove
2018/0310839 A1 11/2018 McCaffrey et al.
2019/0000327 A1 1/2019 Doan
2019/0014993 A1 1/2019 Kaiser
2019/0015103 A1 1/2019 Sharma
2019/0021597 A1 1/2019 Nagy et al.
2019/0021861 A1 1/2019 Finch
2019/0070421 A1 3/2019 Chen

(56) References Cited

U.S. PATENT DOCUMENTS

2019/0150758 A1 5/2019 Bailey et al.
2019/0151122 A1* 5/2019 Kim .......................... A61F 2/07
2019/0167197 A1 6/2019 Abuuassar et al.
2019/0173505 A1 6/2019 Koyama
2019/0175883 A1 6/2019 Wessler et al.
2019/0192864 A1 6/2019 Koop et al.
2019/0254814 A1 8/2019 Nitzan et al.
2019/0262118 A1 8/2019 Eigler et al.
2019/0269392 A1 9/2019 Celermajer et al.
2019/0274855 A1 9/2019 Pate et al.
2019/0298556 A1 10/2019 Bohn et al.
2019/0307459 A1 10/2019 Celermajer et al.
2019/0328513 A1 10/2019 Levi et al.
2019/0336135 A1 11/2019 Inouye et al.
2019/0336163 A1 11/2019 McNamara et al.
2019/0374254 A1 12/2019 Arkvalos et al.
2020/0008870 A1 1/2020 Gruba et al.
2020/0060825 A1 2/2020 Rottenberg et al.
2020/0078196 A1 3/2020 Rosen et al.
2020/0078558 A1 3/2020 Yacoby et al.
2020/0085600 A1 3/2020 Schwartz et al.
2020/0188143 A1 6/2020 McNamara
2020/0196867 A1 6/2020 Andersen et al.
2020/0196876 A1 6/2020 Minor et al.
2020/0196943 A1 6/2020 Minor et al.
2020/0197178 A1 6/2020 Vecchio
2020/0229977 A1 7/2020 Mixter et al.
2020/0229981 A1 7/2020 Mixter et al.
2020/0229982 A1 7/2020 Mixter et al.
2020/0245991 A1 8/2020 Celermajer
2020/0253615 A1 8/2020 Melanson et al.
2020/0260991 A1 8/2020 Rowlaud et al.
2020/0261705 A1 8/2020 Nitzan et al.
2020/0268515 A1 8/2020 Vettukattil et al.
2020/0281611 A1 9/2020 Kelly et al.
2020/0297410 A1 9/2020 Nguyen et al.
2020/0306435 A1 10/2020 Vollmers et al.
2020/0315599 A1 10/2020 Nae et al.
2020/0368505 A1 11/2020 Nae et al.
2020/0391016 A1 12/2020 Passman et al.
2021/0038094 A1* 2/2021 Sweeney .................. A61F 2/86
2021/0038230 A1 2/2021 Larsen et al.
2021/0052378 A1 2/2021 Nitzan et al.
2021/0059527 A1 3/2021 Najafi
2021/0085935 A1 3/2021 Fahey et al.
2021/0100513 A1 4/2021 Sahmauyar et al.
2021/0100665 A1 4/2021 Nae et al.
2021/0121179 A1* 4/2021 Ben-David ............ A61B 5/026
2021/0153776 A1 5/2021 Minar et al.
2021/0177508 A1 6/2021 Kellerman
2021/0205590 A1 7/2021 Fahey et al.
2021/0259732 A1 8/2021 Dicicco et al.
2021/0259829 A1 8/2021 Quinn
2021/0259839 A1 8/2021 Cole et al.
2021/0275733 A1* 9/2021 Goldshtein .......... A61B 5/6869
2021/0290214 A1 9/2021 Cole et al.
2021/0290356 A1 9/2021 Srinkmann et al.
2021/0298763 A1 9/2021 Stahmann et al.
2021/0299425 A1 9/2021 Kume et al.
2021/0299430 A1 9/2021 Ratz et al.
2021/0338990 A1* 11/2021 Eigler ................. A61M 27/002
2021/0361238 A1* 11/2021 Bak-Boychuk ...... A61B 5/6869
2021/0361257 A1 11/2021 Eimer et al.
2021/0370032 A1 12/2021 Fahey et al.
2021/0401418 A1 12/2021 Dang et al.
2022/0008014 A1 1/2022 Rowe et al.
2022/0039670 A1 2/2022 Berrada et al.
2022/0039671 A1 2/2022 Fahey
2022/0061872 A1 3/2022 Mintz
2022/0117555 A1 4/2022 Zarbatauy et al.
2022/0118228 A1 4/2022 Fahey et al.
2022/0143368 A1 5/2022 Pulugurtha et al.
2022/0151618 A1 5/2022 Eigler et al.
2022/0167861 A1 6/2022 Stahmann
2022/0184355 A1 6/2022 Fahey et al.
2022/0192677 A1 6/2022 Wedul et al.
2022/0218355 A1 7/2022 Wedul et al.
2022/0218964 A1 7/2022 Fahey et al.
2022/0226000 A1 7/2022 Alexander et al.
2022/0226623 A1 7/2022 Fahey et al.
2022/0240856 A1 8/2022 Stahmann et al.
2022/0265280 A1 8/2022 Chamorro et al.
2022/0265311 A1* 8/2022 Sorajja ........... A61B 17/320783
2022/0338745 A1 10/2022 Glover et al.
2022/0347446 A1 11/2022 Fahey et al.
2023/0056924 A1 2/2023 Fox et al.
2023/0084193 A1 3/2023 Fahey et al.
2023/0118243 A1 4/2023 Fox et al.
2023/0129883 A1 4/2023 Andriola et al.
2023/0165672 A1 6/2023 Fahey et al.
2023/0191093 A1 6/2023 Nae et al.
2023/0191094 A1 6/2023 Fahey et al.
2023/0201545 A1 6/2023 Alexander et al.
2023/0201546 A1 6/2023 Fahey et al.
2023/0240852 A1 8/2023 Fahey et al.
2023/0372683 A1 11/2023 Andriola et al.
2024/0165381 A1 5/2024 Fahey et al.
2024/0225661 A9 7/2024 Alexander et al.
2024/0335643 A1 10/2024 Andriola et al.
2024/0348482 A1 10/2024 Charthad et al.
2024/0399123 A1 12/2024 Valdez et al.
2024/0416091 A1 12/2024 Mahmoudi

FOREIGN PATENT DOCUMENTS

AU 2011332324 6/2013
AU 2012214279 8/2013
AU 2018228451 9/2019
CA 2785041 8/2011
CA 2786575 8/2011
CA 2818417 5/2012
CA 2955389 1/2016
CA 3054891 9/2018
CN 101415452 4/2009
CN 102458316 5/2012
CN 102905626 1/2013
CN 103458832 12/2013
CN 105662653 6/2016
CN 106456308 2/2017
CN 109646063 4/2019
CN 109646063 A 4/2019
CN 110536657 12/2019
EP 0326757 8/1989
EP 1547549 6/2005
EP 1658818 5/2006
EP 1112044 1/2007
EP 2097012 9/2009
EP 2528646 12/2012
EP 2642954 10/2013
EP 2967867 1/2016
EP 3087953 11/2016
EP 3291773 3/2018
EP 3300672 4/2018
EP 3329860 6/2018
EP 1771132 3/2019
EP 3579907 12/2019
EP 3589238 1/2020
EP 3624701 3/2020
EP 2999412 5/2020
EP 3705154 9/2020
EP 3716877 10/2020
EP 3740163 11/2020
EP 3766431 1/2021
EP 3834737 6/2021
EP 3843618 7/2021
EP 3871626 9/2021
EP 3886761 10/2021
EP 3893731 10/2021
EP 3897369 10/2021
IL 176973 12/2006
IL 221127 9/2012
IL 226374 7/2013
IL 215975 11/2016
IL 227756 6/2017

(56) References Cited

FOREIGN PATENT DOCUMENTS

| | | |
|---|---|---|
| IL | 220201 | 8/2017 |
| IL | 253648 | 9/2017 |
| IL | 255379 | 12/2017 |
| IL | 252395 | 4/2020 |
| IN | 2011KN04472 | 7/2012 |
| IN | 2012KN01275 | 2/2013 |
| IN | 2013KN01954 | 11/2013 |
| IN | 2013CN06525 | 8/2014 |
| IN | 2012KN01988 | 8/2016 |
| JP | 2005177491 | 7/2005 |
| JP | 2007527742 | 10/2007 |
| JP | 2008504878 | 2/2008 |
| JP | 2010508093 | 3/2010 |
| JP | 2012196504 | 10/2012 |
| JP | 2013046784 | 3/2013 |
| JP | 2014503246 | 2/2014 |
| JP | 2014512869 | 5/2014 |
| JP | 2017508581 | 3/2017 |
| JP | 2020509812 | 4/2020 |
| KR | 20010046155 | 6/2001 |
| WO | WO99029227 | 6/1999 |
| WO | WO2001030230 | 5/2001 |
| WO | WO2001072367 | 10/2001 |
| WO | WO2001095783 | 12/2001 |
| WO | WO2003028522 | 4/2003 |
| WO | WO2005074367 | 8/2005 |
| WO | WO2006012038 | 2/2006 |
| WO | WO2007083288 | 7/2007 |
| WO | WO2008055301 | 5/2008 |
| WO | WO2010128501 | 11/2010 |
| WO | WO2010129089 | 11/2010 |
| WO | WO2011093941 | 8/2011 |
| WO | WO2011094521 | 8/2011 |
| WO | WO2012071075 | 5/2012 |
| WO | WO2012085913 | 6/2012 |
| WO | WO2012109557 | 8/2012 |
| WO | WO2013014539 | 1/2013 |
| WO | WO2013096965 | 6/2013 |
| WO | WO2014091222 | 6/2014 |
| WO | WO2014150106 | 9/2014 |
| WO | WO2014188279 | 11/2014 |
| WO | WO2015135955 | 9/2015 |
| WO | WO2016014821 | 1/2016 |
| WO | WO2016038115 | 3/2016 |
| WO | WO2016178171 | 11/2016 |
| WO | WO2018024868 | 2/2018 |
| WO | WO2018132549 | 7/2018 |
| WO | WO2018158747 | 9/2018 |
| WO | WO2019186101 | 2/2019 |
| WO | WO2019142152 | 7/2019 |
| WO | WO2019175401 | 9/2019 |
| WO | WO2019179447 | 9/2019 |
| WO | WO2019188917 | 10/2019 |
| WO | WO2019189079 | 10/2019 |
| WO | WO2019209420 | 10/2019 |
| WO | WO2020023514 | 1/2020 |
| WO | WO2020094085 | 5/2020 |
| WO | WO2020094087 | 5/2020 |
| WO | WO2020094094 | 5/2020 |
| WO | WO2020110048 | 6/2020 |
| WO | WO2020123338 | 6/2020 |
| WO | WO2020132678 | 6/2020 |
| WO | WO2020142515 | 7/2020 |
| WO | WO2020142613 | 7/2020 |
| WO | WO2020198694 | 10/2020 |
| WO | WO2020202046 | 10/2020 |
| WO | WO2020206366 | 10/2020 |
| WO | WO2020215090 | 10/2020 |
| WO | WO2020217194 | 10/2020 |
| WO | WO2020219265 | 10/2020 |
| WO | WO2020225698 | 11/2020 |
| WO | WO2020225757 | 11/2020 |
| WO | WO2020229636 | 11/2020 |
| WO | WO2020234751 | 11/2020 |
| WO | WO2020251700 | 12/2020 |
| WO | WO2020259492 | 12/2020 |
| WO | WO2021025905 | 2/2021 |
| WO | WO2021026485 | 2/2021 |
| WO | WO2021034573 | 2/2021 |
| WO | WO2021046753 | 3/2021 |
| WO | WO2021050589 | 3/2021 |
| WO | WO2021055264 | 3/2021 |
| WO | WO2021065873 | 4/2021 |
| WO | WO2021065874 | 4/2021 |
| WO | WO2021065875 | 4/2021 |
| WO | WO2021065912 | 4/2021 |
| WO | WO2021072315 | 4/2021 |
| WO | WO2021086707 | 5/2021 |
| WO | WO2021091566 | 5/2021 |
| WO | WO2021096766 | 5/2021 |
| WO | WO2021101707 | 5/2021 |
| WO | WO2021113670 | 6/2021 |
| WO | WO2021126699 | 6/2021 |
| WO | WO2021136252 | 7/2021 |
| WO | WO2021136261 | 7/2021 |
| WO | WO2021138041 | 7/2021 |
| WO | WO2021146342 | 7/2021 |
| WO | WO2021150765 | 7/2021 |
| WO | WO2021158559 | 8/2021 |
| WO | WO2021159001 | 8/2021 |
| WO | WO2021162888 | 8/2021 |
| WO | WO2021178636 | 9/2021 |
| WO | WO2021190547 | 9/2021 |
| WO | WO2021212011 | 10/2021 |
| WO | WO2021216964 | 10/2021 |
| WO | WO2021217055 | 10/2021 |
| WO | WO2021217059 | 10/2021 |
| WO | WO2021224736 | 11/2021 |
| WO | WO2022081980 | 4/2022 |
| WO | WO2022266465 | 12/2022 |
| WO | WO2022266503 | 12/2022 |
| WO | WO2022272131 | 12/2022 |
| WO | WO2023278725 | 1/2023 |
| WO | WO2024249425 | 12/2024 |

OTHER PUBLICATIONS

Lehner et al., "The Creation of an Interatrial Right-To-Left Shunt in Patients with Severe, Irreversible Pulmonary Hypertension: Rationale, Devices, Outcomes," Current Cardiology Reports (2019) 21: 31, https://doi.org/10.1007/s11886-019-1118-8; 9 pages.

International Search Report and Written Opinion received for International Application No. PCT/US19/69106 filed Dec. 31, 2019; Applicant: Shifamed Holdings, LLC; Date of Mailing: Mar. 23, 2020; 10 pages.

International Search Report and Written Opinion received for International Application No. PCT/US20/49996 filed Sep. 9, 2020; Applicant: Shifamed Holdings, LLC; Date of Mailing: Feb. 17, 2021; 16 pages.

International Search Report and Written Opinion received for International Application No. PCT/US20/063360 filed Dec. 4, 2020; Applicant: Shifamed Holdings, LLC; Date of Mailing: Apr. 5, 2021; 13 pages.

International Search Report and Written Opinion received for International Application No. PCT/US20/64529 filed Dec. 11, 2020; Applicant: Shifamed Holdings, LLC; Date of Mailing: Apr. 8, 2021; 12 pages.

International Search Report and Written Opinion received for International Application No. PCT/US19/68354, filed Dec. 23, 2019; Applicant: Shifamed Holdings, LLC; Date of Mailing: Mar. 17, 2020; 11 pages.

International Search Report and Written Opinion received for International Application No. PCT/US21/16932, filed Feb. 5, 2021; Applicant: Shifamed Holdings, LLC; Date of Mailing: Jun. 3, 2021; 11 pages.

International Search Report and Written Opinion received for International Application No. PCT/US21/14433, filed Jan. 21, 2021; Applicant: Shifamed Holdings, LLC; Date of Mailing: May 14, 2021; 16 pages.

(56) References Cited

OTHER PUBLICATIONS

International Search Report and Written Opinion received for International Application No. PCT/US21/28926, filed Apr. 23, 2021; Applicant: Shifamed Holdings, LLC; Date of Mailing: Jul. 22, 2021; 16 pages.
International Search Report and Written Opinion received for International Application No. PCT/US20/12059, filed Jan. 2, 2020; Applicant: Shifamed Holdings, LLC; Date of Mailing: Jun. 5, 2020; 12 pages.
International Search Report and Written Opinion received for International Application No. PCT/US20/25509, filed Mar. 27, 2020; Applicant: Shifamed Holdings, LLC; Date of Mailing: Jun. 25, 2020; 9 pages.
International Search Report and Written Opinion received for International Application No. PCT/US20/26738, filed Apr. 3, 2020; Applicant: Shifamed Holdings, LLC; Date of Mailing: Jun. 30, 2020; 8 pages.
International Search Report and Written Opinion received for International Application No. PCT/US21/28931, filed Apr. 23, 2021; Applicant: Shifamed Holdings, LLC; Date of Mailing: Sep. 24, 2021; 20 pages.
International Search Report and Written Opinion received for International Application No. PCT/US21/27747, filed Apr. 16, 2021; Applicant: Shifamed Holdings, LLC; Date of Mailing: Oct. 1, 2021; 16 pages.
International Search Report and Written Opinion received for International Application No. PCT/US21/53836, filed Oct. 6, 2021; Applicant: Shifamed Holdings, LLC; Date of Mailing: Jan. 25, 2022; 20 pages.
International Search Report and Written Opinion received for International Application No. PCT/US21/47573, filed Aug. 25, 2021; Applicant: Shifamed Holdings, LLC; Date of Mailing: Feb. 3, 2022; 15 pages.
Kocaturk, O. et al., “Whole shaft visibility and mechanical performance for active MR catheters using copper-nitinol braided polymer tubes,” Journal of Cardiovascular Magnetic Resonance. Aug. 12, 2009, vol. 11, No. 29, pp. 9, col. 1, In 5-6.
Hossain, M. et al. “In situ preparation of graphene-ZnO composites for enhanced graphite exfoliation and graphene-nylon-6 composite films,” Journal of Applied Polymer Science, Dec. 5, 2016, vol. 134, No. 27, p. 8, In 15-16.
International Search Report and Written Opinion received for International Application No. PCT/US21/55191, filed Oct. 15, 2021; Applicant: Shifamed Holdings, LLC; Date of Mailing: Mar. 1, 2022; 12 pages.
Anomet Products “Conductive Nitinol Wire” Aug. 15, 2020 (Aug. 15, 2020) Retrieved from website <URL: https://helpx.adobe.com/acrobat/using/allow-or-block-links-internet.html?mv=product&mv2=acrobat>, 4 pages.
International Search Report and Written Opinion received for International Application No. PCT/US21/58996, filed Nov. 11, 2021; Applicant: Shifamed Holdings, LLC; Date of Mailing: Feb. 7, 2022; 23 pages.
International Search Report and Written Opinion received for International Application No. PCT/US22/19374, filed Mar. 8, 2022; Applicant: Shifamed Holdings, LLC; Date of Mailing: Jun. 24, 2022; 11 pages.
International Search Report and Written Opinion received for International Application No. PCT/US22/35764, filed Jun. 30, 2022; Applicant: Shifamed Holdings, LLC; Date of Mailing: Sep. 19, 2022; 10 pages.
International Search Report and Written Opinion received for International Application No. PCT/US22/34027, filed Jun. 17, 2022; Applicant: Shifamed Holdings, LLC; Date of Mailing: Oct. 25, 2022; 8 pages.
International Search Report and Written Opinion received for International Application No. PCT/US22/34995, filed Jun. 24, 2022; Applicant: Shifamed Holdings, LLC; Date of Mailing: Nov. 18, 2022; 17 pages.
Perk et al., “Catheter-based left atrial appendage occlusion procedure: role of echocardiography,” published on behalf of the European Society of Cardiology, Sep. 8, 2011, 7 pages.
Collado et al, “Left Atrial Appendage Occlusion for Stroke Prevention in Nonvalvular Atrial Fibrillation,” Journal of the American Heart Association, Jun. 2021, 18 pages.
Extended European Search Report received for Application No. 21892816.6, Applicant: Shifamed Holdings, LLC; Date of Mailing: Jul. 4, 2024; 11 pages.
Extended European Search Report received for Application No. 21881177.6, Applicant: Shifamed Holdings, LLC; Date of Mailing: Sep. 20, 2024; 10 pages.
Extended European Search Report received for Application No. 21878484.1, Applicant: Shifamed Holdings, LLC; Date of Mailing: Sep. 11, 2024; 9 pages.
International Search Report and Written Opinion received for International Application No. PCT/US2024/035748, Applicant: Shifamed Holdings, LLC; Date of Mailing: Oct. 9, 2024; 13 pages.
http://www.collinsdictionary.com/dictionary/english/actuator, actuator definition and meaning, Accessed Oct. 18, 2023, 3 pages.
https://www.ahdictionary.com/word/search.html?q=actuator, American Heritage Dictionary Entry: actuator, Accessed Oct. 18, 2023, 1 page.
https://www.dictionary.com/browse/Actuator, Actuator definition & Meaning, Dictinary.com Accessed Oct. 18, 2023, 1 page.
Extended European Search Report received for Application No. 20896031.0, Applicant: Shifamed Holdings, LLC; Date of Mailing: Dec. 7, 2023; 11 pages.
Huang et al., “Shape Memory Materials,” Science Direct, Materials Today, vol. 13, Sep. 1, 2010, 15 pages.
Retrieved from the Internet: URL:https://www.sciencedirect.com/science/article/pii/S1369702110701280#bib 1, retrieved on Jan. 22, 2024, 1 page.
Extended European Search Report received for Application No. 21791938.0, Applicant: Shifamed Holdings, LLC; Date of Mailing: Apr. 3, 2024; 6 pages.
Ando et al., “Left ventricular decompression through a patent foramen ovale in a patient with hypertrophic cardiomyopathy: a case report,” Cardiovascular Ultrasound volume, Article No. 2 (2004).
Braunwald, Heart Disease, Chapter 6, 2015, p. 186.
Bridges et al., “The Society of Thoracic Surgeons practice guideline series: transmyocardial laser revascularization,” The Annals of Thoracic Surgery, vol. 77, Issue 4, Apr. 2004, pp. 1494-1502.
Bristow et al., “Improvement in cardiac myocyte function by biological effects of medical therapy: A new concept in the treatment of heart failure,” European Heart Journal, vol. 16, Issue suppl. F, Jul. 1995, pp. 20-31.
Case et al., “Relief of High Left-Atrial Pressure in Left-Ventricular Failure,” Lancet, Oct. 17, 1964, pp. 841-842.
Coats et al., “Controlled trial of physical training in chronic heart failure. Exercise performance, hemodynamics, ventilation, and autonomic function,” Circulation, 1992;85:2119-2131.
Davies et al., “Reduced contraction and altered frequency response of isolated ventricular myocytes from patients with heart failure,” Circulation, (1995), 92:2540-2549, Circulation, (1995), 92:2540-2549.
Ennezat et al., “An unusual case of low-flow, low gradient severe aortic stenosis: Left-to-right shunt due to atrial septal defect,” Cardiology, (2009), 113(2):146-148.
Ewert et al., “Masked Left Ventricular Restriction in Elderly Patients With Atrial Septal Defects: A Contraindication for Closure,” Catheterization and Cardiovascular Interventions, 52: 177-180, 2001.
Ewert et al., “Acute left heart failure after interventional occlusion of an atrial septal defect,” Z. Kardiol., Catheterization and Cardiovascular Interventions, Z. Kardiol., (May 2001), 90(5):362-366.
Geiran et al., “Changes in cardiac dynamics by opening an interventricular shunt in dogs,” J. Surg. Res., (Jan. 1990), 48(1):6-12.
Gelernter-Yaniv et al., “Transcatheter closure of left-to-right interatrial shunts to resolve hypoxemia,” Congenit. Heart Dis., (Jan. 2008), 31(1):47-53.

(56) References Cited

OTHER PUBLICATIONS

Gewillig et al., "Creation with a stent of an unrestrictive lasting atrial communication," Cardio. Young, (2002), 12(4):404-407.

Khositseth et al., "Transcatheter Amplatzer Device Closure of Atrial Septal Defect and Patent Foramen Ovale in Patients With Presumed Paradoxical Embolism," Mayo Clinic Proc., 79:35-41 (2004).

Kramer et al., "Controlled study of captopril in chronic heart failure: A rest and exercise hemodynamic study," Circulation, (1983), 67(4):807-816.

Lai et al., "Bidirectional shunt through a residual atrial septal defect after percutaneous transvenous mitral commissurotomy," Cardiology, (1993), 83(3):205-207.

Lemmer et al., "Surgical implications of atrial septal defect complicating aortic balloon valvuloplasty," Ann. thorac. Surg., (Aug. 1989), 48(2):295-297.

Park et al., "Blade atrial septostomy: collaborative study," Circulation, 66(2):258-266 (1982).

Roven et al., "Effect of Compromising Right Ventricular Function in Left Ventricular Failure by Means of Interatrial and Other Shunts," American Journal Cardiology, 24:209-219 (1969).

Salehian et al., "Improvements in Cardiac Form and Function After Transcatheter Closure of Secundum Atrial Septal Defects," Journal of the American College of Cardiology, 45(4):499-504 (2005).

Schmitto et al., "Chronic heart failure induced by multiple sequential coronary microembolization in sheep," The International Journal of Artificial Organs, 31(4):348-353 (2008).

Schubert et al., "Left ventricular conditioning in the elderly patient to prevent congestive heart failure after transcatheter closure of the atrial septal defect," Catheter Cardiovasc. Interv., (2005), 64(3):333-337.

Stormer et al., "Comparative study of in vitro flow characteristics between a human aortic valve and a designed aortic and six corresponding types of prosthetic heart valves," European Surgical Research, (1976), 8(2):117-131.

Stumper et al., "Modified technique of stent fenestration of the atrial septum, Heart," (2003), 89:1227-1230.

Trainor et al., "Comparative Pathology of an Implantable Left Atrial Pressure Sensor," ASAIO Journal, Clinical Cardiovascular/Cardiopulmonary Bypass, 59(5):486-92 (2013).

Zhou et al., "Unidirectional valve patch for repair of cardiac septal defects with pulmonary hypertension," Annals of Thoracic Surgeons, 60: 1245-1249, 1995.

English translation of Japanese Office Action received for JP 2022-515509, Applicant: Shifamed Holdings, Inc., mailed on May 30, 2024, 8 pages.

* cited by examiner

DUAL PURPOSE INDUCTORS FOR IMPLANTABLE MEDICAL DEVICES AND ASSOCIATED SYSTEMS AND METHODS

CROSS-REFERENCE TO RELATED APPLICATION(S)

This application is a 35 U.S.C. § 371 U.S. National Phase application of International Patent Application No. PCT/US2021/055191, filed Oct. 15, 2021, which claims the benefit of U.S. Provisional Application No. 63/093,073, filed Oct. 16, 2020, each of which is incorporated by reference herein in its entirety.

TECHNICAL FIELD

The present technology generally relates to implantable medical devices and, in particular, to implantable systems having dual purpose inductors.

BACKGROUND

Implantable medical devices that can be selectively activated or otherwise actuated generally require some sort of power management system. Some medical devices, for example, include onboard electronics for wirelessly receiving energy and/or charging or recharging an implantable energy storage device (e.g., battery or capacitor). The onboard electronics can include inductors incorporated into various electrical circuits for generating energy in response to exposure to an electric or magnetic field. In order to maximize the inductance of the inductor, the coils are generally orientated in a closely spaced concentrically stacked configuration for maximum coupling efficiency.

DETAILED DESCRIPTION

Figure 1:
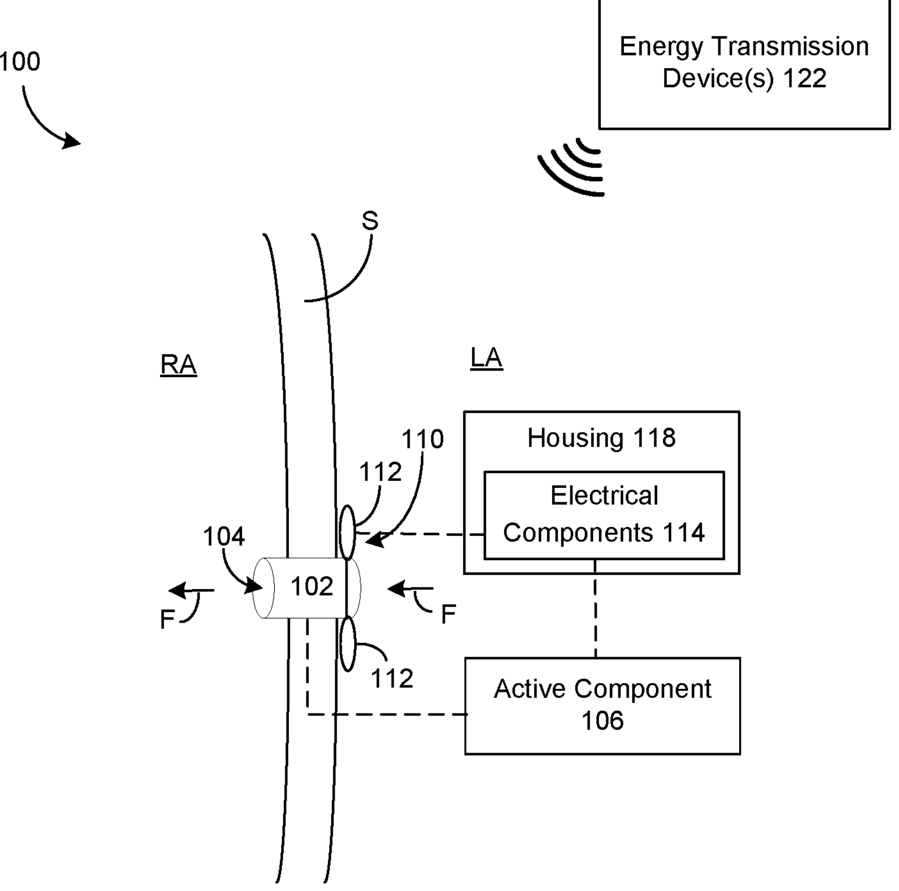
FIG. 1 is a schematic illustration of an interatrial device implanted in a heart and configured in accordance with select embodiments of the present technology.

The present technology is directed to implantable medical devices including an electrical circuit for powering one or more active components of the device, such as an actuation element, an engine, a microcontroller, or a sensor. The electrical circuit can include one or more inductors having one or more receiving wires that generate a current in response to being exposed to an electromagnetic field. As described in detail throughout this Detailed Description, inductors configured in accordance with embodiments of the present technology are designed to generate sufficient energy/power when exposed to an electromagnetic field, even in embodiments in which the inductors are implanted relatively deep in a patient (e.g., in a deep lying body organ, such as a heart). The current generated by the receiving wires can be used to directly or indirectly power the one or more active components. In contrast with conventional inductors, the receiving wires can also be arranged in a non-concentric configuration such that, in addition to generating the current for powering the device, the receiving wires also anchor or stabilize a portion of the device when implanted in a patient. For example, the receiving wires can be at least partially composed of a superelastic material such that they exhibit superelastic properties at body temperature. As discussed further below, an advantage of such a configuration is that the superelastic wires can be easier to deliver and deploy using catheter-based implantation devices, resulting in numerous device functionality and patient safety advantages.

Conventional medical devices with active components that are powered via inductive coupling typically have discrete (i.e., separate) inductive elements (e.g., coils) and anchoring elements. The inductive elements and the anchoring elements are each optimized for their respective functions. For example, the inductive elements are generally composed of a highly conductive material and have a concentrically stacked coiled orientation to maximize the inductance of the element. Anchor elements can take a wide variety of shapes and sizes, but are generally composed of either a rigid, semi-rigid, or superelastic material having a surface area suitable to stabilize the device by engaging patient tissue. Notably, the optimal composition and configuration for inductors is different than the optimal composition and configuration for anchors. Thus, in most conventional devices, inductors do not act as anchors, and vice versa. In contrast with such conventional arrangements, the present technology provides an inductive element that also functions as an anchoring or stabilizing element (referred to herein as a "wire" or "winding").

An additional challenge for many conventional inductor devices is that they are not suitable for use with medical devices implanted relatively deep in a patient (e.g., in the patient's heart as opposed to subcutaneously). For example, many conventional inductors would be unable to generate a sufficient amount of energy/power if implanted relatively deep in the patient unless the patient is exposed to unsafe levels of electromagnetic energy. Moreover, many conventional inductors are relatively large to ensure sufficient charging capabilities, making them unsuitable for transvascular delivery and/or placement within confined cavities. In contrast, and without being bound by theory, implantable medical devices with inductors configured in accordance with the present technology are designed to address one or more of the foregoing challenges. For example, the present technology includes inductors that (1) can be delivered via minimally invasive techniques (e.g., transvascularly via a catheter), (2) can fit within a relatively small cavity (e.g., one or more atria of the patient's heart), and (3) can generate substantial energy/power when exposed to an electromagnetic field that is within acceptable exposure limits.

As set forth above, the inductors described herein can enable charging of an energy storage device that is implanted relatively deep in the human body and/or in a relatively confined space. For example, in one embodiment, the inductor is implemented in a heart failure device such as an interatrial shunt or implantable pressure sensor in which the inductor resides in one or more atria and/or across a septal wall. The shunt may be configured for shunting fluid between a first body region (e.g., a left atrium) and a second body region (e.g., a right atrium) of a patient. The exemplary system includes a shunting element having a lumen extending therethrough that is configured to fluidly couple the first and second body regions when the shunting element is implanted in the patient. The system can further include an actuation element (e.g., a shape memory actuation element) configured to adjust a geometry of the lumen to change the flow of fluid therethrough. Examples of an actuation element for modifying the shunt are described in U.S. patent application Ser. Nos. 16/840,108 and 17/016,192, the entire contents of which are incorporated by reference herein for all purposes. The exemplary system can further include an electrical circuit for providing power to (e.g., to energize in order to induce resistive heating in) the actuation element. The electrical circuit can include one or more inductive wires configured to generate a current when receiving energy (e.g., when positioned in an electromagnetic field). In various embodiments, the inductive wires are configured as antenna and anchors. For example, the wires can induce a current for powering the actuation element and can also anchor and/or stabilize the device (e.g., the shunting element) when it is implanted. In various embodiments, the wires can be at least partially composed of a superelastic material such that they exhibit superelastic properties at body temperature.

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the examples but are not described in detail with respect to FIGS. 1-4.

Reference throughout this specification to “one embodiment” or “an embodiment” means that a particular feature, structure, or characteristic described in connection with the embodiment is included in at least one embodiment of the present technology. Thus, the appearances of the phrases “in one embodiment” or “in an embodiment” in various places throughout this specification are not necessarily all referring to the same embodiment. Furthermore, the particular features or characteristics may be combined in any suitable manner in one or more embodiments.

Reference throughout this specification to relative terms such as, for example, “generally,” “approximately,” and “about” are used herein to mean the stated value plus or minus 10%.

FIG. 1 is a schematic illustration of an exemplary system making use of elements for receiving energy in the body and/or anchoring an implantable medical device. The exemplary system includes an adjustable shunt system 100 (“system 100”) configured in accordance with an embodiment of the present technology. The exemplary system 100 includes a shunting element 102 defining a lumen 104 therethrough. In the illustrated embodiment, the shunting element 102 is implanted across a septal wall S in a patient’s heart, although the shunting element 102 can be implanted in other regions of the body to fluidly connect any two body regions. When implanted across the septal wall S, the system 100 can fluidly connect a left atrium LA and a right atrium RA of the heart via the lumen 104. Accordingly, when the shunting element 102 is implanted in the septal wall S of some patients, blood can flow from the left atrium LA to the right atrium RA via the lumen 104 (as shown by arrows F). The system 100 can further include one or more active components 106 that can be coupled to the shunting element 102. The active component(s) 106 can include any feature implanted with the shunting element 102 that requires energy or power to operate. For example, the active component(s) 106 can include one or more actuation elements (e.g., for adjusting a geometry or other characteristic of the shunting element 102), an engine, a microcontroller, or a sensor (e.g., for measuring one or more physiological parameters and/or one or more parameters of the system 100). The shunting element 102 can include additional features not shown in FIG. 1, such as a frame, membrane, or the like.

The system 100 can further include an energy transmission device(s) 122 for delivering energy (e.g., power) to the implanted components (e.g., the active components 106, the inductor(s) 110, and/or the other electrical components 114, described below) of the system 100. The energy transmission device(s) 122 can include any device or system external to the implant that is capable of wirelessly transmitting energy to an implanted component. For example, the energy transmission device(s) 122 can include a hand-held or portable transmitter, a stationary transmitter (e.g., a mat configured to be placed under the patient’s mattress or in another suitable location, as further described in U.S. Provisional Patent Application No. 63/217,081, the disclosure of which is incorporated herein by reference in its entirety), or other suitable device. The energy transmission device 122 can be configured to transmit radiofrequency (RF) energy, microwave frequency energy, other forms of electromagnetic energy, ultrasonic energy, thermal energy, or other types of energy in accordance with techniques known to those of skill in the art. In some embodiments, the energy transmission device 122 may deliver frequency in a range between about 1 MHz and about 1 GHz, such as between about 1 MHz and about 15 MHz (e.g., 1 MHz, 2 MHz, 3 MHz, 4 MHz, 5 MHz, 6 MHz, etc.), although other frequencies are possible. In some embodiments, the energy transmission device 122 may generate an electromagnetic field directed toward the implanted aspects of the system 100. For example, the energy transmission device 122 may generate a substantially uniform electromagnetic field surrounding the system 100. Optionally, the energy transmission device(s) 122 can include one or more devices configured to be positioned at least temporarily within the patient’s body (e.g., an energy delivery catheter configured to be navigated proximate to the system 100 during a procedure).

The system 100 can further include onboard electronics, including one or more inductors 110 and other electrical components 114 (e.g., capacitors, resistors, etc.) electrically coupled together to form electric circuits (e.g., RLC resonant circuits, as described below with respect to FIG. 3). The inductor(s) 110 can include one or more receiving wires 112 (also referred to herein as “inductive elements,” “inductor coils” or “inductor wires”) that can receive energy (e.g., power) from the energy transmission device 122. For example, in some embodiments, the inductor wire(s) 112 generates energy in response to exposure to an electromagnetic field created by the energy transmission device 122. The generated energy can be used to power the active component(s) 106, as described below with respect to FIG. 2. The wire(s) 112 can have a circular cross-sectional shape, a rectangular cross-sectional shape, or any other suitable cross-sectional shape.

As described in greater detail with reference to FIGS. 2A-2C, the one or more wires 112 can form a plurality of loops, petals, or the like. However, unlike conventional inductors, the wire(s) 112 generally has a non-concentric configuration such that the plurality of loops or petals do not have a "stacked" configuration in which a center point of a first coil is axially aligned with a center point of a second coil. In some embodiments, the inductor 110 is formed by a single, continuous wire 112. In other embodiments, the inductor 110 is formed by multiple wires 112 connected in series (e.g., soldered or otherwise joined together in an end-to-end configuration). Regardless of whether the inductor 110 is composed of a single wire 112 or multiple wires 112, the wire(s) 112 forms an electrically continuous inductive structure that possesses substantial inductance throughout its length. As described in further detail below with reference to FIGS. 2A-2C, this is expected to provide several advantages relative to systems that incorporate a plurality of discrete inductors and/or an inductor that has portions separated by segments having relatively low inductance and relatively high resistance. The wire(s) 112 are also arranged so that the current flow is in the same sense (e.g., direction). Moreover, although the wire(s) 112 is shown as being positioned at a first region of the system 100 (e.g., in the left atrium LA), in some embodiments, such as described with reference to FIGS. 2B and 2C, the wire(s) 112 can be configured to extend across the septal wall S such that a portion of the inductor 110 is positioned at a second opposite region of the system (e.g., in the right atrium RA).

In addition to generating energy for powering various aspects of the system 100, the wire(s) 112 can also be configured to anchor and/or stabilize the shunting element 102 or another aspect of the system 100 in a desired position (the inductor 110 and/or the wire(s) 112 can therefore also be referred to herein as an "anchoring assembly"). In one embodiment, for example, the individual wire(s) 112 can engage with patient tissue (e.g., the septal wall S as shown in FIG. 1) to secure the shunting element 102 in position. For example, as illustrated in FIG. 1, the inductor wire(s) 112 can be arranged non-concentrically to form a plurality of spaced apart individual coils, loops, petals, or the like. This arrangement is in contrast with conventional inductor configurations, in which the inductor wires are coiled in a closely spaced, concentrically stacked configuration. As a result, the contact area of the wire(s) 112 is increased compared to a single coil with multiple overlaid turns.

The inductor wire(s) 112 can have a composition that further increases the stabilization provided by the wire(s). In some embodiments, the inductor wire(s) 112 can be at least partially composed of a superelastic material (e.g., nitinol) such that it exhibits an elastic response to applied stress at body temperature. For example, the wire(s) 112 can have a highly conductive (e.g., silver) core surrounded by a superelastic (e.g., nitinol) sheath or coating. As another example, the wire(s) 112 can have a superelastic core (e.g., having a relatively high resistivity) with a highly conductive sheath or coating (e.g., having a relatively low resistivity and/or that is malleable). As yet another example, the wire(s) 112 can include a highly conductive wire coupled to a superelastic wire, or another suitable arrangement. The superelastic properties of the wire(s) 112 enables the wire(s) 112 to resist plastic mechanical deformation and thus can provide a generally stable anchoring mechanism for the shunting element 102 or other aspect of the system 100, while the conductive properties enable the wire(s) 112 to function as a high quality factor inductor. In some embodiments, an insulating material (e.g., a bio-compatible polymer such as polyurethane, polytetrafluoroethylene, etc.) can be positioned around the wire(s) 112 to reduce the impact of proximity effect relative to coils made with more closely spaced conductors.

As will be understood by one of skill from the description herein, the wire(s) 112 may be formed of material other than superelastic materials. A variety of materials are suitable for the wire(s) 112 including, but not limited to elastomers, metals, and alloys, and more. The shape and configuration of the wire(s) 112 may be determined based on the material properties, delivery technique, and/or requirements of the application. In various embodiments, the wire(s) 112 is configured to be delivered surgically or minimally invasively (e.g., mini thoracotomy). In various embodiments, the wire(s) 112 is configured to be delivery percutaneously through a catheter. The materials and configuration of certain embodiments of the wire(s) 112 will be described in more detail below.

In addition to stabilizing/anchoring one or more aspects of the system 100, the wire(s) 112 can also be used to position the electrical components 114 or other components of the system 100 in a desired position during deployment of the system 100. For example, the electrical components 114 can be contained within a housing or can 118 mechanically coupled to the wire(s) 112. During delivery, the wire(s) 112 may be compressed, crimped, or otherwise deformed to be placed within a catheter. Upon deployment from the catheter at a target implant site, the superelastic properties of the wire(s) 112 will cause the wire(s) 112 to expand to their deployed configuration, such as that shown in FIG. 1. Because the wire(s) 112 is mechanically coupled to the housing 118, the housing 118 will be directed to a predetermined position as the wire(s) 112 expand into its deployed configuration.

Figure 2A:
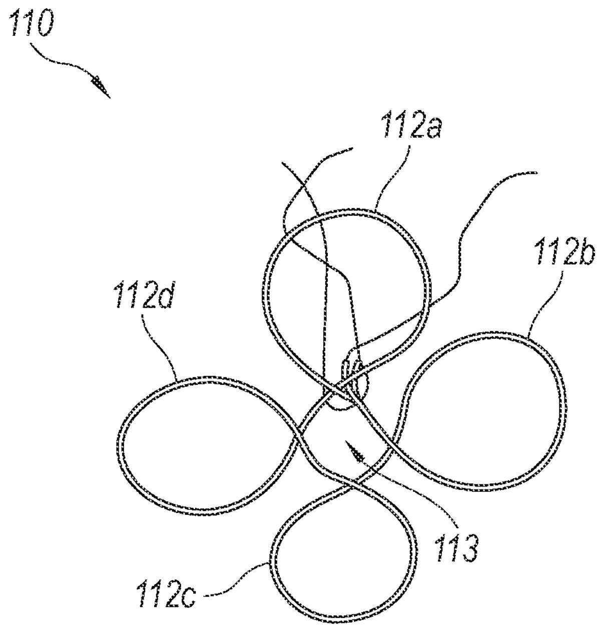
FIG. 2A is a schematic illustration of an inductor configured in accordance with select embodiments of the present technology.

FIG. 2A illustrates additional details of a first embodiment of the inductor 110 configured in accordance with select embodiments of the present technology. As illustrated, in some embodiments the inductor 110 includes a wire 112 forming a plurality of wire loops 112 (four are shown as wire loops 112*a*-112*d*). The wire loops 112*a*-112*d* are oriented in a flower-petal or clover-like configuration (as opposed to the conventional concentrically stacked/helical configuration) such that the center points of the wire loops 112*a*-112*d* generally do not overlap. The wire loops 112*a*-112*d* can extend from or otherwise surround the shunting element 102 (e.g., as best shown in FIG. 1). For example, the wire 112 can define a core region 113 that can be coupled to or otherwise surround the shunting element 102 or other component of the system 100. The wire loops 112*a*-112*d* can therefore provide an anchoring mechanism for the shunting element 102, with each wire loop 112*a*-112*d* contacting a different portion of the septal wall S.

Although shown as a single wire having four wire loops 112*a*-112*d*, one skilled in the art will appreciate that the inductor 110 can have any number of wires, can have any number of loops or petals formed by the wire(s), and can be arranged in any suitable configuration for anchoring the shunting element 102 while maintaining sufficient inductance for receiving and/or generating energy. For example, the inductor 110 can include one, two, three, four, five, six, seven, eight, nine, ten, or more wires coupled in series in an end-to-end configuration. As another example, each wire loop 112*a*-112*d* of the inductor 110 may include more than a single receiving wire (e.g., loop 112*a* can comprise two or more similarly shaped stacked wires, loop 112*b* can comprise two or more similarly shaped stacked wires, etc.). As yet another example, the system 100 can include multiple inductors 110 (two, three, four, five, six, seven, eight, or more) coupled in series in the same electrical circuit.

Figure 2B:
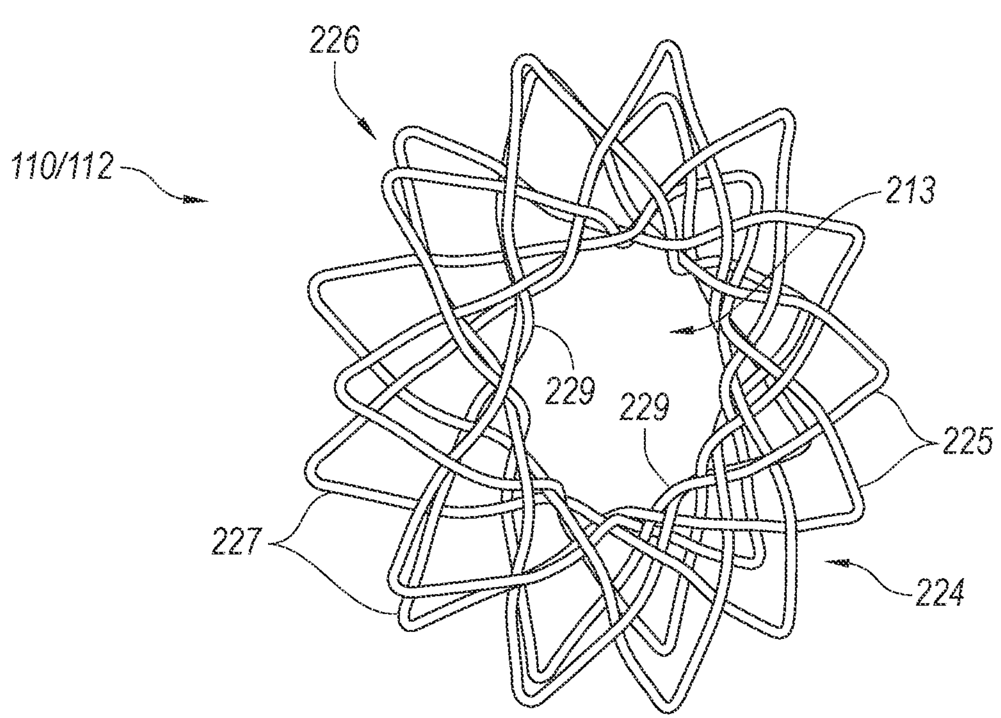
FIGS. 2B-2D illustrate another inductor configured in accordance with select embodiments of the present technology.
Figure 2C:
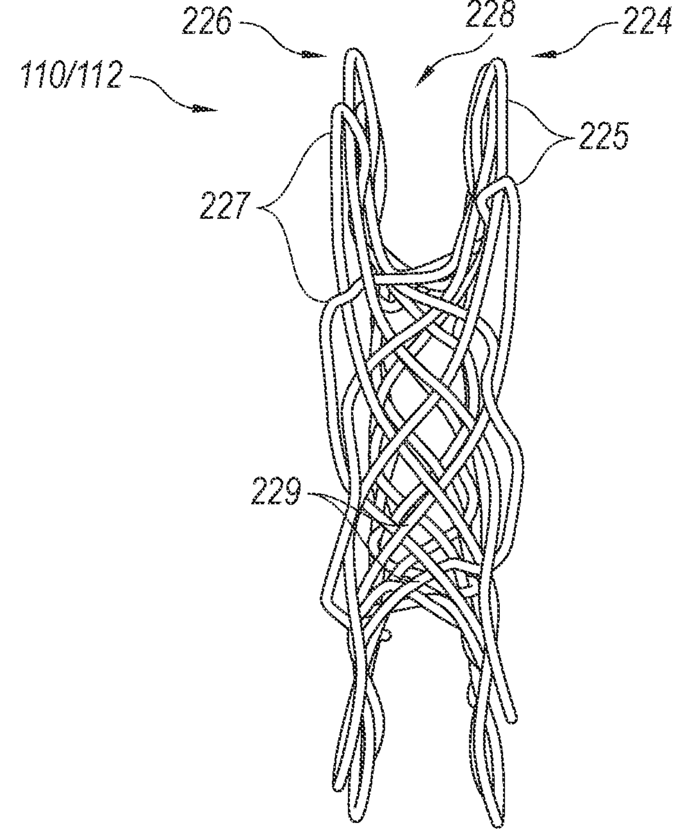
Figure 2D:
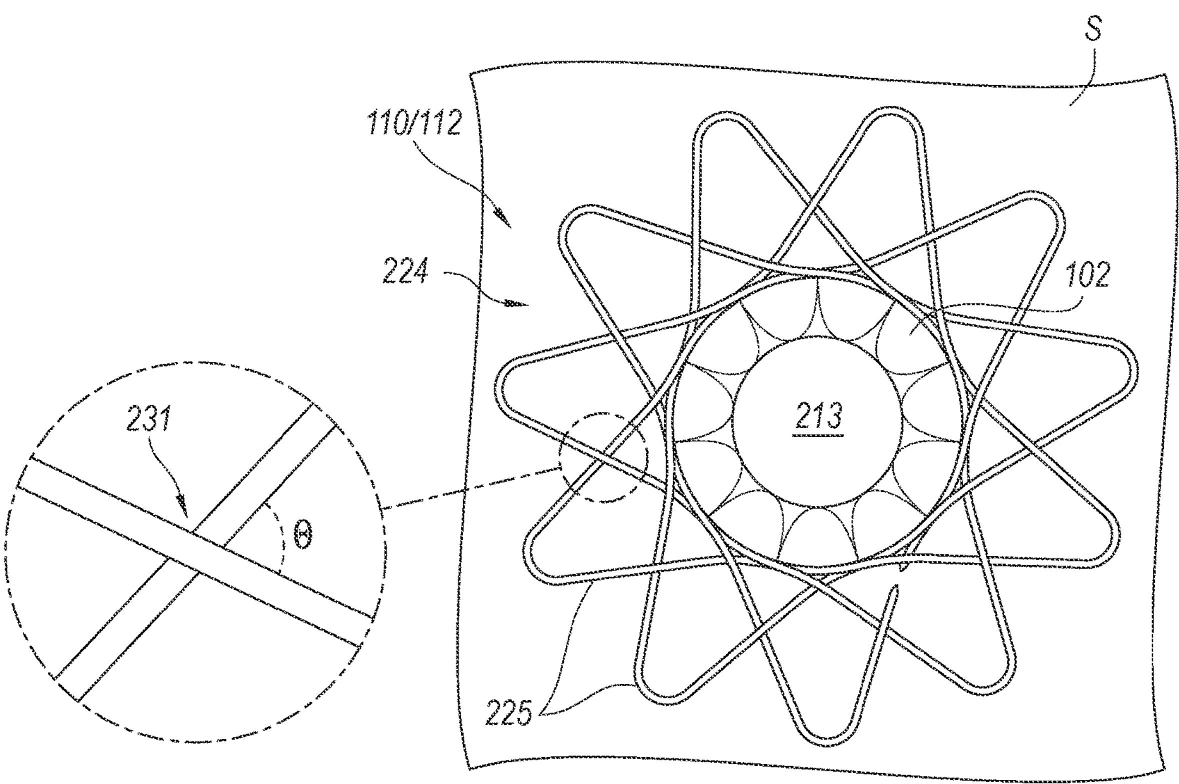

FIGS. 2B-2D illustrate another embodiment of the inductor 110 configured in accordance with select embodiments of the present technology. As shown in FIGS. 2B and 2C, the inductor 110 can be formed by a single continuous wire 112 that is woven into a torsional or annular shape having a central aperture 213 extending therethrough. The inductor 110 can have a first end region 224 at which the wire 112 forms a plurality of first petals or loops 225, and a second end region 226 at which the wire 112 forms a plurality of second petals or loops 227. The first petals 225 and the second petals 227 can be joined by connecting segments 229 that extend between the first end region 224 and the second end region 226. As best shown in FIG. 2C, the first petals 225 and the second petals 227 can be spaced apart by a gap 228. In operation, tissue (e.g., the septal wall) can be received within the gap 228, and the first petals 225 and the second petals 227 can apply a slightly inward pressure relative to the gap 228 (e.g., by virtue of the superelasticity of the wire 112) to stabilize or secure the inductor 110 and one or more components of the system 100 (FIG. 1) to the tissue. FIG. 2D, for example, is a front view of the inductor 110 deployed across a septal wall S, illustrating the first petals 225 of the first end region 224 engaging the septal wall S and defining the aperture 213 extending therethrough. In the illustrated embodiment, the inductor 110 is stabilizing the shunting element 102 across the septal wall S, although in other embodiments the shunting element 102 can be omitted and the inductor 110 can stabilize other components (e.g., a sensor).

Referring back to FIGS. 2B-2D together, the wire 112 can have a woven, mesh-like, or braided pattern or configuration in which segments of the wire 112 "cross" or "overlap" one another. For example, as best shown in the enlarged portion of FIG. 2D, the wire 112 forms a plurality of intersections 231 at which segments of adjacent petals of the plurality of first petals 225 cross one another. Of note, in some embodiments, the wire 112 is configured such that the segments of the wire(s) 112 forming the intersection 231 form an angle θ of between about 30 degrees and about 150 degrees, between about 45 degrees and about 135 degrees, between about 70 degrees and 110 degrees, between about 80 degrees and about 100 degrees, or about 90 degrees. In some embodiments, overlapping segments of the connecting portion 229 of the wire(s) 112 (FIG. 2C) also form an angle θ of between about 30 degrees and about 150 degrees, between about 45 degrees and about 135 degrees, between about 70 degrees and 110 degrees, between about 80 degrees and about 100 degrees, or about 90 degrees. This is in contrast with inductors in which the overlapping segments are parallel or have angles θ of less than about 30 degrees. Without being bound by theory, inductors 110 that have normal or substantially normal overlapping segments (e.g., overlapping segments with the angle θ being between about 30 degrees and about 150 degrees) as compared to inductors 110 that have parallel or substantially parallel overlapping segments (e.g., overlapping segments with the angle θ being less than about 30 degrees) are expected to advantageously demonstrate (1) reduced self-capacitance, and/or (2) reduced effects of the proximity effect, which disadvantageously increases resistance of the inductor 110. As a result, the inductor 110 can have a relatively higher number of turns, coils, loops or the like while maintaining low resistance and a self-resonant frequency substantially greater than the power transfer frequency. Lower resistance and a higher self-resonant frequency both increase the voltage produced across the inductor. In some embodiments, the wire(s) 112 can include an insulating material (e.g., a bio-compatible polymer) at least at the intersections 231 to further reduce the impact of the proximity effect.

Although primarily described as a single continuous wire 112, in some embodiments the inductor 110 can be composed of a plurality of wires 112 soldered or otherwise joined together in an end-to-end configuration, as previously described. However, even in embodiments in which the inductor 110 is formed of a plurality of wires 112 joined in an end-to-end configuration, the inductor 110 is a single, electrically continuous inductive structure that possesses substantial inductance throughout its length (e.g., the inductor 110 is designed to eliminate or at least minimize conductor paths across the wire(s) 112 that add resistance without significantly contributing to the inductance). Without being by bound theory, this is expected to ensure that a ratio between inductance and resistance is maintained within a suitable range and/or above a suitable threshold that enables the inductor 110 to generate electrical current when exposed to an electromagnetic field. For example, in some embodiments the value of $2\times\pi\times f\times L/R$ is preferentially in the range 40-100, where L is the inductance of the inductor in Henries, R is the resistance of the inductor in Ohms, and f is the power transfer frequency in Hz. Distributing inductance throughout the entirety of the inductor 110 is also expected to minimize inductance variation that may arise due to mechanical deformation of the inductor 110 resulting from anatomical variations and movements (e.g., pulsatile motions) at the deployment site.

Without being bound by theory, the inductor(s) 110 having a receiving wire(s) 112 configured in non-concentrically stacked orientations as described with reference to FIGS. 1-2D may have less inductance than if the same receiving wires were arranged in the conventional concentrically stacked coiled configuration. For example, non-overlapping wires have an inductance that is generally 1/N compared to the same wires if concentrically stacked, where N is the number of non-overlapping wire loops (e.g., N=2 if there are two non-overlapping wire loops, in which case the inductance is ½ of what it would be if the two wire loops were concentrically stacked). Accordingly, the non-concentrically stacked wires 112 may have an inductance about 5% less than, about 10% less than, about 15% less than, about 20% less than, about 30% less than, about 40% less than, about 50% less than, about 60% less than, about 70% less than, about 80% less than, or about 90% less than if the same wires were coiled in the conventional stacked configuration. The wires 112 nevertheless generate sufficient energy in response to the electromagnetic field in order to power the one or more active components 106. For example, and without being bound by theory, generating a substantially uniform electromagnetic field using the energy transmission device 122 enables the inductor wire(s) 112 to generate sufficient energy in the resonant RLC circuit to power the one or more active components 106. Moreover, the wire(s) 112 are designed to generate sufficient energy in response to an electromagnetic field that is within acceptable (e.g., clinically acceptable) exposure limits. Acceptable exposure limits are generally expressed as a range for magnetic field-frequency product, for example in the range of 2-20 uT·MHz. In one embodiment, a representative exposure limit could be 0.3-3 uT at 6.78 MHz.

Figure 3A:
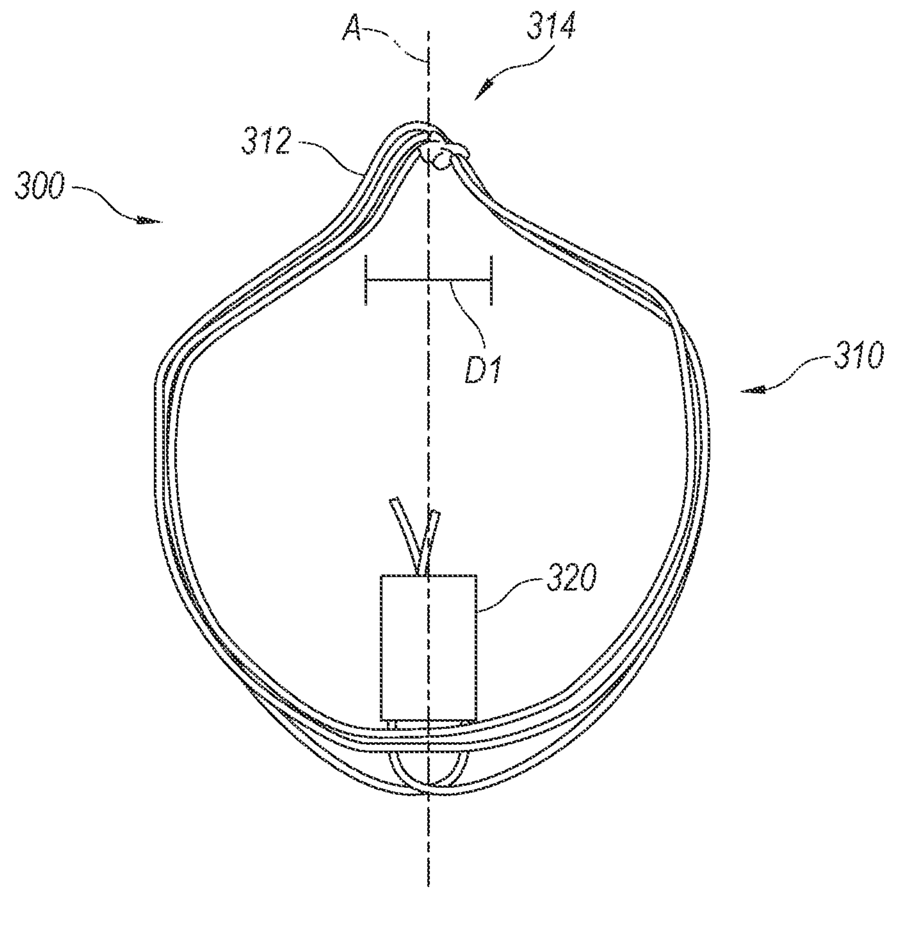
FIGS. 3A and 3B illustrate aspects of an implantable medical device configured in accordance with select embodiments of the present technology.
Figure 3B:
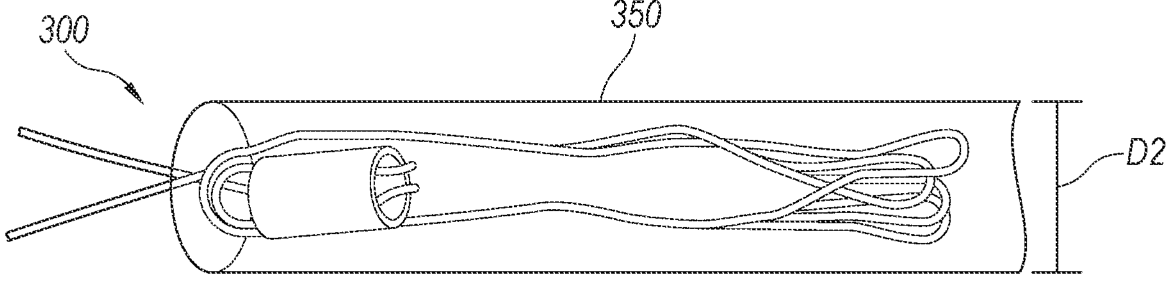

FIGS. 3A and 3B illustrate select aspects of an implantable medical device 300 configured in accordance with embodiments of the present technology. In particular, FIG. 3A illustrates a view of the device 300 in a deployed configuration, and FIG. 3B illustrates a view of the device 300 in a delivery configuration. Referring first to FIG. 3A, the device 300 includes an inductive element 310 comprising one or more receiving or inductive wires 312 (which can be a single continuous inductive wire or multiple inductive wires coupled in series, and may also be referred to as "coils" or "receiving wires"). The inductive wires 312 can be composed of any of the materials previously described herein, such as composite materials having a superelastic material and a highly conductive material. In the deployed configuration, the inductive wires 312 have a surface area sufficient to engage patient tissue to anchor/stabilize the device 300 in a desired position. The device 300 further includes a housing or can 320 configured to house one or more electrical components of the device 300. The device 300 can further include a body element, such as the shunting element 102 described with respect to FIG. 1.

Unlike the embodiment described with respect to FIGS. 1 and 2, the inductive wires 312 can be "stacked" such that a plurality of wire segments are overlapping. However, relative to conventional inductive coils, the inductive wires 312 have a greater circumference (e.g., 25% greater, 50% greater, 100% greater, etc.). In some embodiments, such as the illustrated embodiment, the inductive wires 312 also have a non-circular and/or non-oval shape in the deployed configuration. For example, the inductive wires 312 may have a height (parallel to the long axis A) that is greater than its width (perpendicular to the long axis A). In other embodiments, the inductive wires 312 may have a width that is greater than its height. The ratio between the height and width of inductive wires can be about 2:1, 1.9:1, 1.8:1, 1.7:1, 1.6:1, 1.5:1, 1.4:1, 1.3:1, 1.2:1, 1.1:1, 1:1, 0.9:1, 0.8:1, 0.7:1, 0.6:1, 0.5:1, 0.4:1, 0.3:1, or 0.2:1. The desired dimensions/ratio can be selected based on where the device 300 is to be implanted. For example, in embodiments in which the device 300 includes a septal shunt and the inductive wires 312 will anchor the system against the septal wall, the inductive wires 312 may have a height of about 40 mm and a width of about 30 mm. The non-circular geometries can therefore enable the inductive wires 312 to engage a greater surface area of patient tissue, which is expected to maximize power transfer and improve the stabilization provided by the inductive wires 312.

The inductive wires 312 can also form a folding element, such as a nub or projection 314. The nub 314 can be oriented about a long axis A of the device 300 to facilitate collapse (e.g., using less force) of the device into a delivery configuration that can fit within a catheter 350, shown in FIG. 3B. The nub 314 can also facilitate deployment (e.g., using less force) of device 300 from the catheter 350. The nub 314 can also alter the stress and/or strain distributions within the wires 312, which can facilitate its collapse into a delivery configuration (e.g., as shown in FIG. 3B). In particular, the nub 314 can have a dimension D1 that is less than an inner diameter D2 of the catheter 350, such that when collapsed, the system fits within the catheter 350. Although shown as having a single nub 314, the device 300 can optionally include a plurality of nubs 314, for example a second nub oriented along the long axis A (e.g., positioned at the bottom portion of the device 300).

Because of their non-circular geometries, the inductive wires 312 can also act as a positioning element during deployment of the device 300. For example, various components of the device 300 (e.g., the can 320) can be oriented along the long axis A of the inductive wires 312. Accordingly, a physician can adjust an orientation of the inductive wires 312 to adjust an orientation of the components aligned with its long axis A. This is expected to be particularly beneficial in embodiments in which the physician can visualize the inductive wires 312 but not the other components (e.g., if the device 300 is being implanted across a septal wall and the inductive wires 312 are in the right atrium, the physician may be able to visualize the wires 312 via a catheter-mounted camera, but not other components of the system in the left atrium).

Figure 4:
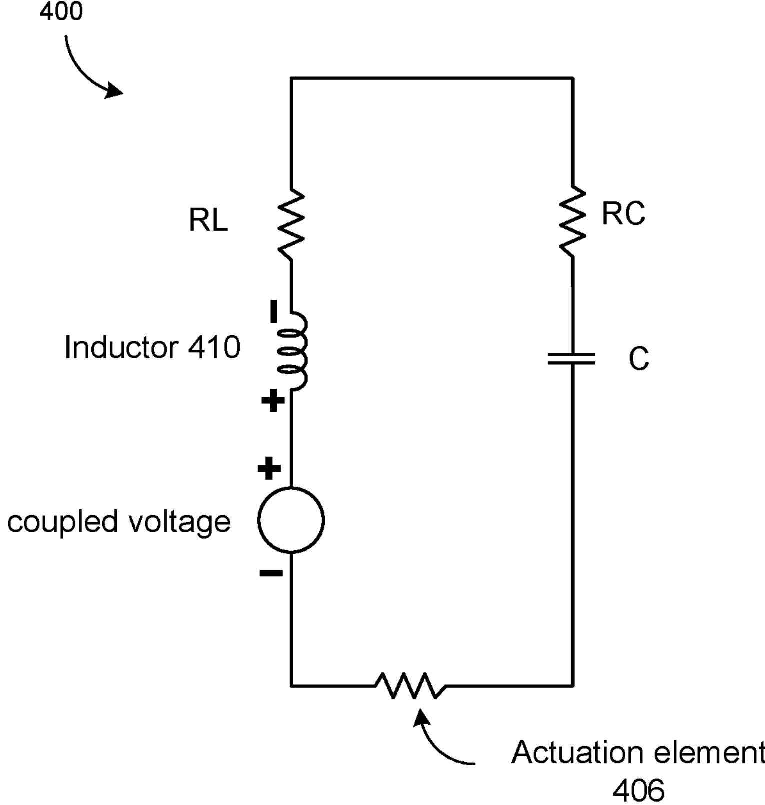
FIG. 4 is a schematic illustration of an electrical circuit configured in accordance with select embodiments of the present technology.

As provided above, and in addition to forming anchors, the inductive elements described herein (e.g., the inductor wires 112 of the system 100 and the inductor wires 312 of the device 300) are integrated into electrical circuits that are used to power the one or more active components 306. FIG. 4, for example, is a circuit diagram of an exemplary resonant RLC circuit 400 formed using an inductor wire 410 (which can be the same as the inductor wires 112 or the inductor wire 312), the electrical components 114 (which can include the capacitor C in FIG. 4), and an active component (shown in FIG. 4 as an actuation element 406) in accordance with an embodiment of the present technology. In embodiments in which the actuation element 406 is composed of a shape memory material, the actuation element 406 can be powered through resistive heating and does not require a specific energy waveform like many conventional motors or engines. As a result, the actuation element 406 can be directly incorporated into the resonant RLC circuit 400. For example, in the illustrated embodiment, the actuation element 406 is coupled in series with the other electrical components of the resonant RLC circuit 400. When the resonant RLC circuit 400 is activated (e.g., via the external energy transmission device(s) 122—FIG. 1), current flows through the actuation element 406, resistively heating the actuation element 406. In embodiments in which the actuation element 406 is composed of a shape memory material, this resistive heating may heat the shape memory actuation element above its transition temperature and drive the material phase transformation that induces a geometry change in the lumen 104, as described in detail above with respect to FIG. 1. Additional details of exemplary resonant RLC circuits that incorporate an actuation element and can be used with the inductors described herein are described in International Patent Application No. PCT/US21/53836, filed Oct. 6, 2021, the disclosure of which is incorporated by reference herein in its entirety.

As one skilled in the art will appreciate from the disclosure herein, the inductor(s) 410 can be incorporated in other electrical circuits beyond those illustrated in FIG. 4. For example, the inductor(s) 410 can be incorporated into a conventional RLC circuit that provides power to an energy storage device (e.g., a supercapacitor, a battery, etc.), which can subsequently release the stored energy to power an active component (e.g., motor, sensor, etc.). As one skilled in the art will further appreciate, the power/energy generated by the inductors described herein can vary based on a number of factors, including the strength of the electromagnetic field or other energy source, the duration of exposure, etc. For example, in some embodiments the inductors described herein are configured to receive between about 5 mW and about 500 mW of power during daily/weekly/monthly maintenance charging. In some embodiments, the inductors can further be configured to receive between about 5 W and about 20 W of power to enable certain tasks that require more energy (e.g., to enable adjustment of a shunt during a clinic visit).

The combination of inductive elements and anchoring elements in the same component as described herein offers several advantages over technologies that are presently available. As described previously, traditional systems utilize coiled inductive components and anchor/stabilization components that are separate and discrete from one another. This adds complexity to the system and increases the system's overall size and weight, which may not be suitable for certain confined anatomical locations, such as within one or more atria of a patient's heart. In contrast, devices incorporating the present technology can be relatively smaller in size, which can benefit patients by leaving more room around the implant (e.g., more room on a septal wall) to enable future procedures (e.g., pulmonary vein ablation, mitral valve procedures, left atrial appendage closures, etc.). Moreover, devices configured in accordance with the presently disclosed technology are expected to be more robust to failure.

Traditional coil systems also complicate the delivery of implants and components. For example, cardiovascular implants are often delivered through small catheters. Traditional coil materials (e.g., silver, copper, gold, etc.) that are relatively soft and malleable can be collapsed into a catheter for delivery, but may be difficult to re-form into an appropriate coil shape upon delivery. Wires (e.g., coils) comprised of superelastic materials (e.g., nitinol manufactured to be in a austenitic material state at body temperature) may be easier to deliver as they can "self-deploy" when they are unsheathed, but the electrical properties of such materials can render these wires inefficient and/or unsuitable for use as energy receiving coils for an implanted device (e.g., to act as coils in a system to drive an actuator). Use of wires comprised of composite materials (e.g., a wire composed of nitinol coated with a more conductive silver layer) can strike a balance between electrical performance and mechanical delivery practicality. As presently disclosed, using wires composed of composite materials allow for a wire component to act as both a self-deploying anchor and an energy receiving component, which can enable a smaller implant and therefore a smaller catheter delivery size, which increases the safety profile for patients. Indeed, one of the expected advantages of the present technology is that the systems described herein can be delivered and deployed using a standard 24 Fr (or smaller) catheter.

As one of skill in the art will appreciate from the disclosure herein, various components of the systems described above can be omitted without deviating from the scope of the present technology. Likewise, additional components not explicitly described above may be added to the systems without deviating from the scope of the present technology. Moreover, the electrical circuits described herein can be incorporated into other types of implantable medical devices beyond cardiac shunts. Accordingly, the present technology is not limited to the configurations expressly identified herein, but rather encompasses variations and alterations of the described systems.

EXAMPLES

Several aspects of the present technology are set forth in the following examples:

1. A system for shunting fluid between a first body region and a second body region, the system comprising:
   - a shunting element having a lumen extending therethrough and configured such that, when the shunting element is implanted in the patient, the lumen fluidly connects the first body region and the second body region;
   - an actuation element configured to adjust a geometry of the lumen; and
   - an electrical circuit for powering the actuation element, the electrical circuit including a wire configured to—
     - generate current when exposed to an electromagnetic field, and
     - anchor the shunting element in a target position when the shunting element is implanted in a patient.
2. The system of example 1 wherein the electrical circuit is a resonant RLC circuit.
3. The system of example 1 or 2 wherein the wire is configured to (1) form at least a first loop or petal in the first body region, (2) form a second loop or petal in the second body region, and (3) receive tissue between the at least first loop or petal and the at least second loop or petal to anchor the system in the target position.
4. The system of example 3 wherein the wire is a single wire.
5. The system of example 3 wherein the wire includes a plurality of wires arranged in series.
6. The system of any of examples 1-5 wherein the wire forms a plurality of non-overlapping loops.
7. The system of any of examples 1-5 wherein the wire includes stacked wire segments having a non-circular shape.
8. The system of example 7 wherein the stacked wire segments have a non-oval shape.
9. The system of any of examples 1-8 wherein the wire is composed of a superelastic material and a highly conductive material.
10. The system of example 9 wherein the superelastic material is nitinol and the highly conductive material is silver.
11. The system of example 9 wherein the wire includes a superelastic core and an inductive exterior.
12. The system of example 9 wherein the wire includes an inductive core and a superelastic exterior.
13. The system of any of examples 1-12 wherein the wire serves as the only anchor element in an anatomical region.
14. An electrical circuit for use with an implantable medical device, the electrical circuit comprising:
    - an inductor coupled to the implantable medical device, wherein the inductor includes a wire that, when deployed across a tissue wall of a patient, forms at least one first loop or petal on a first side of the tissue wall and at least one second loop or petal on a second side of the tissue wall,
    - wherein the wire is configured to—
      - generate current when exposed to an electromagnetic field, and
      - receive a portion of the tissue wall between the first loop or petal and the second loop or petal to anchor the device in a target position when the device is implanted in a patient.
15. The electrical circuit of example 14 wherein the electrical circuit is a resonant RLC circuit.
16. The electrical circuit of example 14 or 15 wherein the wire is a single wire.
17. The electrical circuit of example 14 or 15 wherein the wire includes a plurality of wires arranged in series.
18. The electrical circuit of any of examples 14-17 wherein the wire forms a plurality of non-overlapping loops.
19. The electrical circuit of any of examples 14-17 wherein the wire includes stacked wire segments having a non-circular shape.
20. The electrical circuit of example 19 wherein the stacked wire segments have a non-oval shape.
21. The electrical circuit of any of examples 14-20 wherein the wire is composed of a superelastic material and a highly conductive material.

22. The electrical circuit of example 21 wherein the superelastic material is nitinol and the highly conductive material is silver.
23. The electrical circuit of example 21 wherein the wire includes a superelastic core and an inductive exterior.
24. The electrical circuit of example 21 wherein the wire includes an inductive core and a superelastic exterior.
25. The electrical circuit of any of examples 14-24 wherein the at least one first loop or petal includes a first first petal and a second first petal both configured to reside on the first side of the tissue wall, the first first petal and the second first petal having overlapping segments that form an angle of between about 30 degrees and about 150 degrees.
26. The electrical circuit of any of examples 14-25 wherein the wire serves as the only anchor element in an anatomical region.
27. An inductor for use with an implantable medical device configured to be implanted across a tissue wall separating a first body region and a second body region, the inductor comprising:

one or more wires composed of a composite material including a highly conductive material and a superelastic material, wherein the one or more wires form a single electrically continuous inductive structure having a first plurality of loops or petals, a second plurality of loops or petals at least partially spaced apart from the first plurality of loops or petals by a gap, and plurality of connecting segments extending between the first plurality of loops or petals and the second plurality of loops or petals, wherein, when the inductor is implanted in a patient, the first end region is configured to reside within the first body region, the second end region is configured to reside within the second body region, and the gap is configured to receive a portion of the tissue wall.

28. The inductor of example 27 wherein individual first loops or petals of the first plurality of loops or petals do not overlap.
29. The inductor of example 27 wherein individual first loops or petals of the first plurality of loops or petals overlap.
30. The inductor of example 29 wherein the individual first loops or petals have a height and a width, and wherein the height is greater than the width.
31. The inductor of any of examples 27-30 wherein the one or more wires form a folding element or nub for compressing the one or more wires into a delivery configuration.
32. The inductor of any of examples 27-31 wherein the wire serves as the only anchor element in an anatomical region.
33. A method of treating a patient, the method comprising:

advancing a catheter carrying a heart failure treatment device through the patient's vasculature and toward the patient's heart, the heart failure treatment device including an anchoring assembly formed by a continuous inductive structure having one or more wires;

deploying the heart failure treatment device from the catheter at a target location in the patient's heart, wherein, upon deployment from the catheter, the continuous inductive structure automatically expands into a deployed position and stabilizes the heart failure treatment device at the target location; and charging one or more energy storage components on the heart failure treatment device by generating an electromagnetic field, wherein the continuous inductive structure generates an electrical current in response to being exposed to the electromagnetic field.

34. The method of example 33 wherein the continuous inductive structure is formed by a single wire.
35. The method of example 33 or 34 wherein the continuous inductive structure includes a superelastic core and an inductive exterior.
36. The method of any of examples 33-35 wherein, once deployed, the one or more wires form one or more overlapping segments, wherein each overlapping segment forms an angle between about 30 degrees and about 150 degrees.
37. The method of any of examples 33-36 wherein the heart failure treatment device includes a sensor.
38. The method of any of examples 33-36 wherein the heart failure treatment device includes an interatrial shunt.

CONCLUSION

Embodiments of the present disclosure may include some or all of the following components: a battery, supercapacitor, or other suitable power source; a microcontroller, FPGA, ASIC, or other programmable component or system capable of storing and executing software and/or firmware that drives operation of an implant; memory such as RAM or ROM to store data and/or software/firmware associated with an implant and/or its operation; wireless communication hardware such as an antenna system configured to transmit via Bluetooth, WiFi, or other protocols known in the art; energy harvesting means, for example a coil or antenna which is capable of receiving and/or reading an externally-provided signal which may be used to power the device, charge a battery, initiate a reading from a sensor, or for other purposes. Embodiments may also include one or more sensors, such as pressure sensors, impedance sensors, accelerometers, force/strain sensors, temperature sensors, flow sensors, optical sensors, cameras, microphones or other acoustic sensors, ultrasonic sensors, ECG or other cardiac rhythm sensors, SpO2 and other sensors adapted to measure tissue and/or blood gas levels, blood volume sensors, and other sensors known to those who are skilled in the art. Embodiments may include portions that are radiopaque and/or ultrasonically reflective to facilitate image-guided implantation or image guided procedures using techniques such as fluoroscopy, ultrasonography, or other imaging methods. Embodiments of the system may include specialized delivery catheters/systems that are adapted to deliver an implant and/or carry out a procedure. Systems may include components such as guidewires, sheaths, dilators, and multiple delivery catheters. Components may be exchanged via over-the-wire, rapid exchange, combination, or other approaches.

The above detailed description of embodiments of the technology are not intended to be exhaustive or to limit the technology to the precise forms disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments. For example, although this disclosure has been written to describe devices that are generally described as being used to create a path of fluid communication between the left atrium and the right atrium, it should be appreciated that similar embodiments could be utilized for shunts between other chambers of the heart or for shunts in other regions of the body.

Unless the context clearly requires otherwise, throughout the description and the examples, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. An implantable medical device, comprising:

an active component; and an inductor, wherein the inductor includes a wire that, when deployed across a tissue wall of a patient, forms at least one first loop or petal on a first side of the tissue wall configured to contact the tissue wall on the first side, and at least one second loop or petal on a second side of the tissue wall configured to contact the tissue wall on the second side, wherein the at least one first loop or petal extends generally parallel to the at least one second loop or petal, wherein the wire is configured to— generate an electrical current when exposed to an electromagnetic field to directly or indirectly provide power to the active component, and receive a portion of the tissue wall between the first loop or petal and the second loop or petal to anchor the active component in a target position when the implantable medical device is implanted in a patient.

2. The implantable medical device of claim 1 wherein the inductor is part of a resonant RLC circuit.

3. The implantable medical device of claim 1 wherein the wire is a single wire.

4. The implantable medical device of claim 1 wherein the wire includes a plurality of wires arranged in series.

5. The implantable medical device of claim 1 wherein the wire forms a plurality of non-overlapping loops.

6. The implantable medical device of claim 1 wherein the wire includes stacked wire segments having a non-circular shape.

7. The implantable medical device of claim 6 wherein the stacked wire segments have a non-oval shape.

8. The implantable medical device of claim 1 wherein the wire is composed of a superelastic material and a highly conductive material.

9. The implantable medical device of claim 8 wherein the superelastic material is nitinol and the highly conductive material is silver.

10. The implantable medical device of claim 8 wherein the wire includes a superelastic core and an inductive exterior.

11. The implantable medical device of claim 8 wherein the wire includes an inductive core and a superelastic exterior.

12. The implantable medical device of claim 1 wherein the at least one first loop or petal includes a first first petal and a second first petal both configured to reside on the first side of the tissue wall, the first first petal and the second first petal having overlapping segments that form an angle of between about 30 degrees and about 150 degrees.

13. The implantable medical device of claim 1 wherein the wire serves as the only anchor element in an anatomical region.

14. The implantable medical device of claim 1 wherein the active component includes a shape memory actuation element.

15. The implantable medical device of claim 1 wherein the active component includes a sensor.

16. An implantable medical device configured to be implanted across a tissue wall separating a first body region and a second body region, the implantable medical device comprising:

an active component; and an inductor configured to be implanted across the tissue wall, wherein the inductor includes one or more wires composed of a composite material including a highly conductive material and a superelastic material, wherein the one or more wires form a single electrically continuous inductive structure having a first plurality of loops or petals oriented within a first plane, a second plurality of loops or petals at least partially spaced apart from the first plurality of loops or petals by a gap and oriented in a second plane that is generally parallel to the first plane, and a plurality of connecting segments extending between the first plurality of loops or petals and the second plurality of loops or petals, wherein, when the inductor is implanted in a patient, a first end region with the first plurality of loops or petals is configured to reside within the first body region, a second end region with the second plurality of loops or petals is configured to reside within the second body region, and the gap is configured to receive a portion of the tissue wall, and wherein the inductor is configured to (i) anchor or stabilize the active component, and (ii) generate an electrical current when exposed to an electromagnetic field to directly or indirectly power the active component.

17. The implantable medical device of claim 16 wherein individual first loops or petals of the first plurality of loops or petals do not overlap.

18. The implantable medical device of claim 16 wherein individual first loops or petals of the first plurality of loops or petals overlap.

19. The implantable medical device of claim 18 wherein the individual first loops or petals have a height and a width, and wherein the height is greater than the width.

20. The implantable medical device of claim 16 wherein the one or more wires form a folding element or nub for compressing the one or more wires into a delivery configuration.

21. The implantable medical device of claim 16 wherein the wire serves as the only anchor element in an anatomical region.

22. The implantable medical device of claim 16 wherein the active component includes a shape memory actuation element.

23. The implantable medical device of claim 16 wherein the active component includes a sensor.

* * * * *